(12) United States Patent
Wittwer et al.

(10) Patent No.: US 9,771,610 B2
(45) Date of Patent: *Sep. 26, 2017

(54) PRIMERS FOR MELTING ANALYSIS

(71) Applicants: University of Utah Research Foundation, Salt Lake City, UT (US); BioFire Defense, LLC, Salt Lake City, UT (US)

(72) Inventors: Carl T. Wittwer, Salt Lake City, UT (US); Luming Zhou, Salt Lake City, UT (US); Mark Aaron Poritz, Salt Lake City, UT (US)

(73) Assignees: University of Utah Research Foundation, Salt Lake City, UT (US); BioFire Defense, LLC, Salt Lake City, UT (US)

( * ) Notice: Subject to any disclaimer, the term of this patent is extended or adjusted under 35 U.S.C. 154(b) by 1024 days.

This patent is subject to a terminal disclaimer.

(21) Appl. No.: 13/770,539

(22) Filed: Feb. 19, 2013

(65) Prior Publication Data

US 2016/0348157 A1 Dec. 1, 2016

Related U.S. Application Data

(63) Continuation of application No. 12/530,052, filed as application No. PCT/US2008/056217 on Mar. 7, 2008, now Pat. No. 8,399,189.

(Continued)

(51) Int. Cl.
*C12Q 1/68* (2006.01)
*C07H 21/02* (2006.01)

(52) U.S. Cl.
CPC ......... *C12Q 1/6816* (2013.01); *C12Q 1/6818* (2013.01); *C12Q 1/6827* (2013.01); *C12Q 1/6858* (2013.01)

(58) Field of Classification Search
CPC ........ C12Q 2525/301; C12Q 2527/107; C12Q 2531/107; C12Q 1/6816; C12Q 1/6827; C12Q 1/6858; C12Q 1/6818
See application file for complete search history.

(56) References Cited

U.S. PATENT DOCUMENTS 7,297,484 B2 11/2007 Wittwer et al.
7,387,887 B2 6/2008 Wittwer et al.
(Continued)

FOREIGN PATENT DOCUMENTS

WO 03072810 9/2003
WO 2007035806 3/2007

OTHER PUBLICATIONS

Aktipis et al., "Thermal Denaturation of the DNA-Ethidium Complex Redistribution of the Intercalated Dye During Melting," Biochemistry 1975; 14:326-31.
(Continued)

*Primary Examiner* — Teresa Strzelecka
(74) *Attorney, Agent, or Firm* — Workman Nydegger

(57) ABSTRACT

Methods and kits are provided for nucleic acid analysis. In an illustrative method a target nucleic acid is amplified using a first primer and a second primer, wherein the first primer comprises a probe element specific for a locus of the target nucleic acid and a template-specific primer region, and the probe element is 5' of the template-specific primer region, subsequently allowing the probe element to hybridize to the locus to form a hairpin, generating a melting curve for the probe element by measuring fluorescence from a dsDNA binding dye as the mixture is heated, wherein the dye is not covalently bound to the first primer, and analyzing the shape of the melting curve. Kits may include one or more of the first and second primers, the dsDNA binding dye, a polymerase, and dNTPs.

28 Claims, 19 Drawing Sheets

Related U.S. Application Data

(60) Provisional application No. 60/905,721, filed on Mar. 8, 2007.

(56) References Cited

U.S. PATENT DOCUMENTS

| | | | |
|---|---|---|---|
| 7,456,281 | B2 | 11/2008 | Dujols |
| 7,582,429 | B2 | 9/2009 | Wittwer et al. |
| 8,399,189 | B2 | 3/2013 | Wittwer et al. |
| 2005/0053950 | A1 | 3/2005 | Zudaire et al. |
| 2005/0233335 | A1* | 10/2005 | Wittwer .......... C09B 23/04 435/6.18 |
| 2007/0020656 | A1 | 1/2007 | Sorge |
| 2009/0117553 | A1 | 5/2009 | Wittwer et al. |

OTHER PUBLICATIONS

Aoshima et al. "Rapid Detection of Deletion Mutations in Inherited Metabolic Diseases by Melting Curve Analysis with LightCycler" Clin. Chem. 2000 46:119-22.

Douthart et al. "Binding of Ethidium Bromide to Double-Stranded Ribonucleic Acid," Biochemistry 1973; 12:214-20.

Highsmith et al. "Use of a DNA Toolbox for the Characterization of Mutation Scanning Methods. I: Construction of the Toolbox and Evaluation of Heteroduplex Analysis," Electrophoresis 1999, 20:1186-1194.

Hladnik et al. "Single-Tube Genotyping of MBL-2 Polymorphisms Using Melting Temperature Analysis" Clin. Exp. Med. 2002; 2:105-108.

Howell et al. "iFRET: An Improved Fluorescence System for DNA-Melting Analysis" Genome Res. 2002, 12:1401-7.

Itoga et al. "Comparative Analyses of Four Different Methods of Genotyping ALDH2" Alcoholism: Clin. Exp. Res., vol. 28, pp. 117S-122S, 2004.

Lee et al. "Allelic Discrimination by Nick-Translation PCR with Fluorogenic Probes" Nucleic Acids Research, Aug. 11, 1993, 21(16); 3761-6.

Lipsky et al. "DNA Melting Analysis for Detection of Single Nucleotide Polymorphisms" Clin. Chem. 2001; 47:635-44.

Margraf et al. "Masking Selected Sequence Variation by Incorporating Mismatches into Melting Analysis Probes" Hum. Mut. vol. 27, pp. 269-278, Jan. 2006.

Marziliano et al. "Melting Temperature Assay for a UGTIA Gene Variant in Gilbert Syndrome" Clin. Chem. 2000, 46:423-55.

Pirulli et al. "Flexibility of Melting Temperature Assay for Rapid Detection of Insertions, Deletions, and Single-Point Mutations of the AGXT Gene Responsible for Type 1 Primary Hyperoxaluria" Clin. Chem. 2000; 46:1842-44.

Pont-Kingdon et al. "Direct Molecular Haplotyping by Melting Curve Analysis of Hybridization Probes; Beta 2-Adrenergic Receptor Haplotypes as an Example" Nucl. Acids Res. 2005, 33:e89.

Pramanik et al. "Hairpin Fomation in DNA Fragments CCAATTTGG, CCAATTTTTGG, and CCATTTTGG: A Proton NMR Study" Biochem., vol. 27, pp. 3024-3031, 1988.

Reed "Sensitivity and Specificity of Single-Nucleotide Polymorphism Scanning by High-Resolution Melting Analysis" Clin. Chem. 2004, 50:1748-54.

Shendure et al. "Accurate Multiplex Polony Sequencing of an Evolved Bacterial Genome" Science 2005; 309:1728-32.

Solinas et al. "Duplex Scorpion Primers in SNP Analysis and FRET Applications" Nucleic Acids Research, 2001, 29:E96.

Tanriverdi et al. "Detection and Genotyping of Oocysts of Cryptosporidium Parvum by Real-Time PCR and Melting Curve Analysis" J. Clin. Microbiol. 2002, 40:3237-44.

Thelwell et al. "Mode of Action and Application of Scorpion Primers to Mutation Detection" Nucleic Acids Research, 2000, 28:3752-61.

Von Ahsen et al. "Limitations of Genotyping Based on Amplicon Melting Temperature," Clinical Chemistry 2001, vol. 47, No. 7, p. 1331-1332.

Wei et al. "Detection of Known Thalassemia Point Mutations by Snapback Single-Strand Conformation Polymorphism: The Feasibility Analysis" ScienceDirect Clinical Biochemistry, 2006, 36:833-842.

Wetmur et al. "Molecular Haplotyping by Linking Emulsion PCR; Analysis of Paraxonase 1 Haplotypes and Phenotypes" Nucliec Acids Research, 2005, 33:2615-9.

Whitcombe et al. "Detection of PCR Products Using Self-Probing Amplicons and Fluorescence" Nature Biotechnology vol. 17, pp. 804-807, 1999.

Wilton et al. "Snapback SSCP Analysis: Engineered Conformation Changes for the Rapid Typing of Known Mutations" Human Mutations vol. 11, pp. 252-258, 1998.

Wittwer et al. "High-Resolution Genotyping by Amplicon Melting Analysis Using LCGreen" Clin. Chem. 2003, 49:853-60.

Wittwer et al. "Real-Time Multiplex PCR Assays" Methods, 2001, 25:430-42.

Wittwer et al. "Real-Time PCR" in Persing et al. "Diagnostic and Molecular Microbiology: Principles and Applications" ASM Press, 2004.

Wittwer et al. "Continuous Fluorescence Monitoring of Rapid Cycle DNA Amplification" Biotechniques, 1997; 22:130-1, 4-8.

Zhou et al. "Closed-Tube Genotyping with Unlabeled Oligonucleotide Probes and a Saturating DNA Dye" Clinical Chemistry, vol. 50, pp. 1328-1335, 2004.

Zhou et al. "High-Resolution DNA Melting Analysis for Simultaneous Mutation Scanning and Genotyping in Solution" Clin. Chem. 2005, 51(10) pp. 1770-1777.

International Search Report and Written Opinion for PCT/US2008/056217 dated Sep. 10, 2008.

U.S. Appl. No. 12/530,052, Feb. 24, 2012, Office Action.
U.S. Appl. No. 12/530,052, Aug. 17, 2012, Office Action.
U.S. Appl. No. 12/530,052, Nov. 29, 2012, Notice of Allowance.

\* cited by examiner

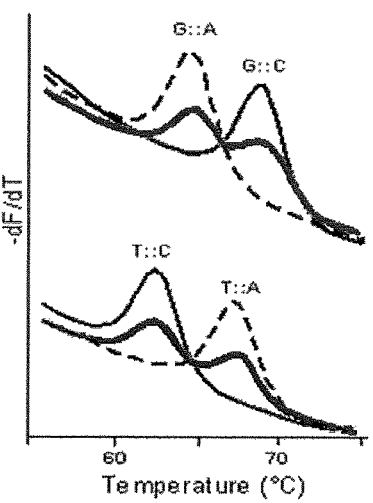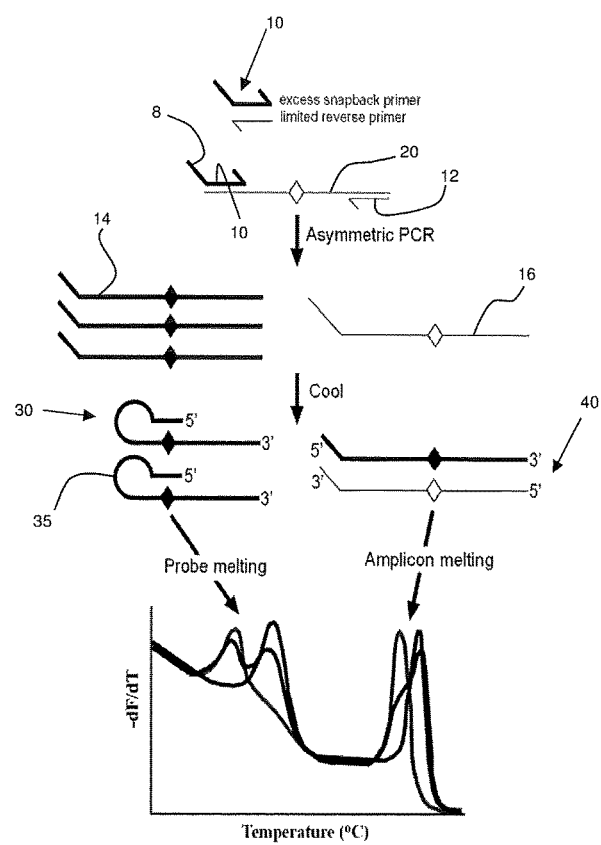

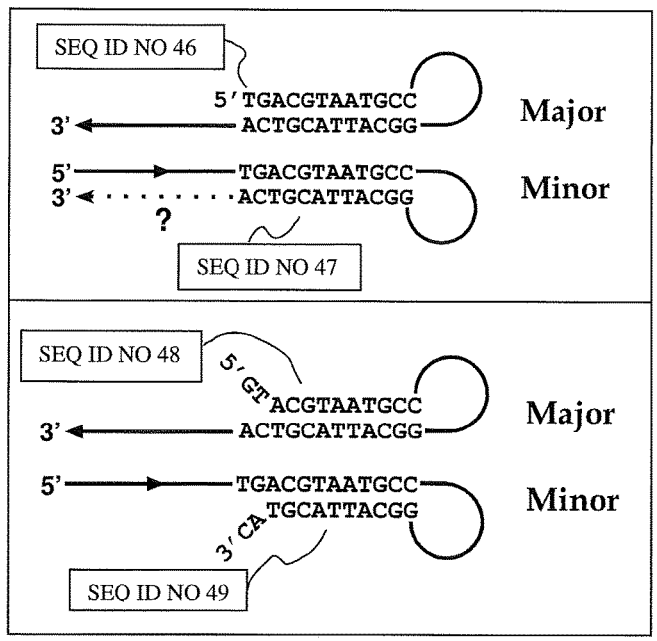
Fig. 7A
Fig. 7B
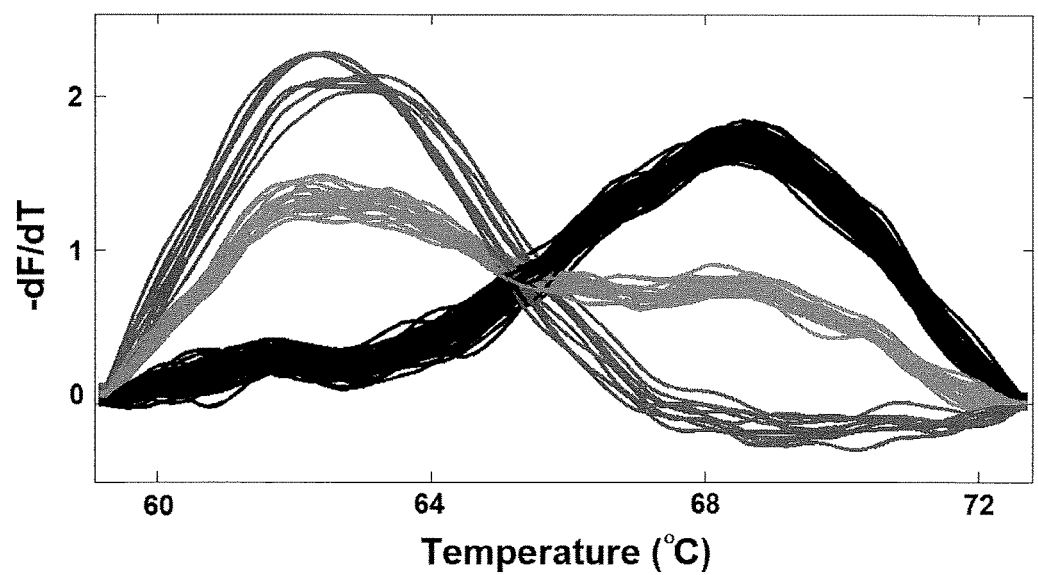
Fig. 7C

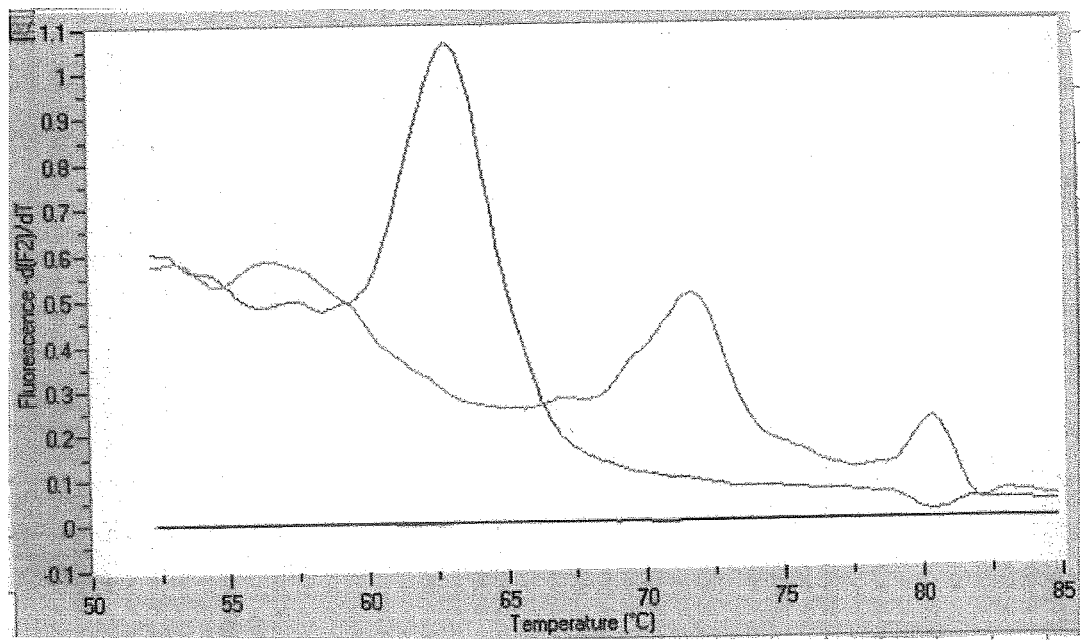
Fig. 16
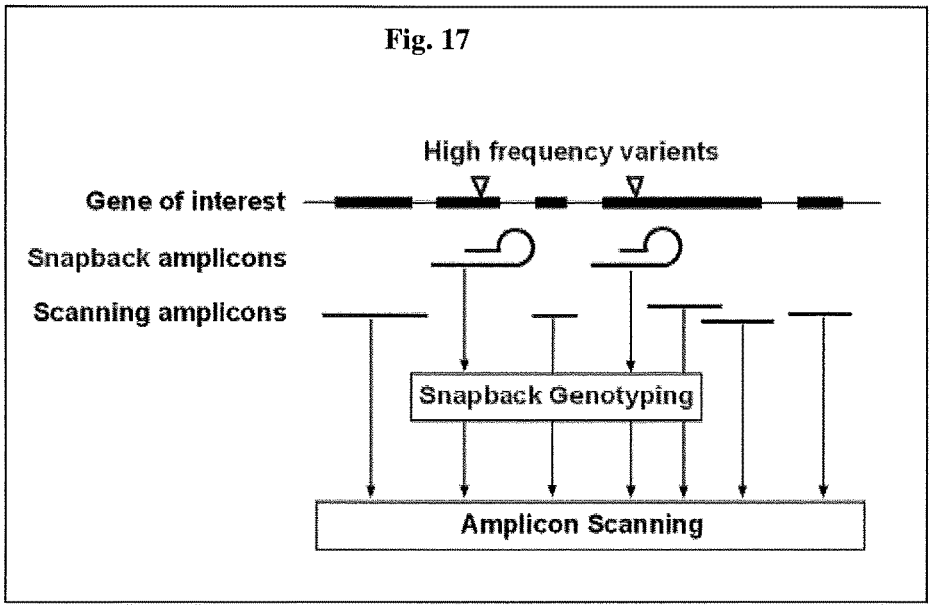

PRIMERS FOR MELTING ANALYSIS

PRIORITY

This application is a continuation of U.S. application Ser. No. 12/530,052 filed on Apr. 1, 2010, which is a national stage application of PCT Application Serial No. PCT/US2008/56217, filed on Mar. 7, 2008; which claims priority from U.S. Application Ser. No. 60/905,721, filed on Mar. 8, 2007, the entire disclosure of which is incorporated herein by reference.

BACKGROUND OF THE INVENTION

The human genome project has succeeded in sequencing most regions of human DNA. Work to identify the genes and sequence alterations associated with disease continues at a rapid pace. Linkage studies are used to associate phenotype with genetic markers such as simple sequence repeats or single nucleotide polymorphisms (SNPs) to identify candidate genes. Sequence alterations including SNPs, insertions, and deletions that cause missense, frameshift, or splicing mutations then may be used to pinpoint the gene and the spectrum of responsible mutations.

However, even when the genetic details become known, it is difficult to use this knowledge in routine medical practice, in large part because the methods to analyze DNA are expensive and complex. When costs are significantly lowered and the methods dramatically simplified, it is expected that DNA analysis will become accessible for use in everyday clinical practice for effective disease detection and better treatment. Ideal DNA analysis is rapid, simple, and inexpensive.

When a disease is caused by a limited number of mutations, or when a few sequence alterations constitute a large proportion of the disease cases, direct genotyping is feasible. Traditional methods range from classical restriction digestion of PCR products to closed-tube fluorescent methods. Closed-tube methods of DNA analysis can be simple to perform. Once PCR is initiated, no further reagent additions or separations are necessary. However, closed-tube methods are traditionally expensive, due in large part to the cost of the fluorescent probes used. Although there are many elegant designs, the probes are often complex with multiple fluorescent dyes and/or functional groups. For example, one popular approach uses a fluorescent dye and a quencher, each covalently attached to an allele-specific probe (1). Two of these "TaqMan®" probes are required to genotype one SNP. Not only are the probes costly, but the time required for hybridization and exonuclease cleavage also limits the speed at which PCR can be performed.

Another example of closed-tube genotyping uses Scorpion® primers, available from DxS Ltd. Originally described in 1999, Scorpion® primers, or "self-probing amplicons," are formed during PCR from a primer that includes a 5'-extension comprising a probe element, a pair of self complementary stem sequences, a fluorophore/quencher pair, and a blocking monomer to prevent copying the 5'-extension (2). As illustrated in FIG. 1, in the original stem-loop format, the probe element forms the loop, and the stem brings the fluorophore and quencher into close proximity. After PCR, the probe element hybridizes to a portion of the extension product, opening up the stem and separating the fluorophore from the quencher. An additional duplex format, also illustrated in FIG. 1, was later developed in which the fluorophore on the Scorpion® primer is quenched by a quencher on a separate complementary probe that forms a duplex before PCR (3). After PCR, the probe element, which is now part of the amplicon, separates from the quenching probe and hybridizes to the amplicon. In both cases, probing is an intramolecular reaction.

There are several advantages of intramolecular reactions over intermolecular probes. First, intramolecular hybridization is fast and is not a limiting step, even with the current fastest PCR protocols (4). The probe element is stabilized by the intramolecular reaction, increasing probe melting temperatures by about 5-15° C., so that shorter probes can be used, illustratively in areas of high sequence variation. In the stem-loop format, a single oligonucleotide serves both as one of the primers and as a probe. However, such probes can be complex and expensive. The high cost is driven by the high complexity to produce certain probes. For example, each Scorpion® primer requires three modifications to the oligonucleotide primer (a fluorophore, a quencher, and a blocker). A closed-tube genotyping system that retains the advantages of Scorpion® primers, but eliminates their complexity and cost, would be desirable.

Yet another method for genotyping, "Snapback single strand conformation polymorphism, or SSCP", has been used. SSCP uses a primer of a specific sequence to introduce secondary structure into PCR products that are later separated by electrophoresis to reveal single strand conformation polymorphisms ("SSCP") (5). In Snapback SSCP, a complementary 8-11 bp primer tail loops back on its complementary sequence in the extension product, creating a hairpin in the single stranded amplicon, which is later detected by gel separation.

As discussed above, Snapback primers may be used to introduce a secondary loop structure into an extension product. However, Snapback primers and other prior art methods discussed herein rely on post-amplification gel separation, or use expensive fluorescently labeled primers. In comparison, the methods of the present invention use a dsDNA dye and melting analysis to monitor hybridization of the hairpin. According to one aspect of the present application, after PCR, illustratively but not limited to asymmetric PCR, intramolecular melting of the hairpin allows genotyping. The intramolecular hybridization is illustrated in FIG. 2. The method is simple because only two PCR primers are required, the only addition being a 5'-tail of nucleotides on at least one primer. No covalent fluorophores, quenchers or blockers are required, greatly reducing the cost of synthesis and assay development. Thus, in one illustrative embodiment, the dsDNA dye is untethered and is free to bind and be released from the nucleic acid solely based on melting.

One issue that has prevented a better method of genotyping revolves around the fact that most genetic diseases are complex. Many different sequence alterations in the same or different genes may contribute to a disease phenotype. The initial hope that most human diseases are caused by a handful of sequence variants has proven not to be true. Many genes can contribute to a particular phenotype, and many different mutations within a gene may cause the same or similar disease patterns. Therefore, to determine the link between a genotype and its resultant phenotype, genetic testing often requires parallel analysis of many coding and regulatory regions. Several methods of screening DNA for abnormalities are available and are known as "scanning" methods. While "genotyping" focuses on detecting specific sequence alterations, mutation scanning can flag the presence of an abnormality, which can then be identified through methods such as genotyping or sequencing.

Sequencing is currently the gold standard for identifying sequence variation. Even though costs are decreasing, sequencing is still a complex process that is not rapid, simple, or inexpensive when applied to specific genetic diagnosis or pharmacogenetics. This remains true for methods that use polonies (6) or emulsion PCR (7). Standard sequencing requires seven steps: 1) amplification bp PCR, 2) clean up of the PCR product, 3) addition of cycle sequencing reagents, 4) cycle sequencing for dideoxy termination, 5) clean up of the termination products, 6) separation by capillary electrophoresis, and 7) data analysis. This complexity can be automated and has been in some sequencing centers, but sequencing still remains much more complex than the methods of the present invention. Further, when large or multiple genes are analyzed, over 90% of the sequenced products come back normal. A simple method that could identify normal sequences and common variants would eliminate most of the time, cost, and effort of sequencing.

Snapback primers of the present invention may be used to integrate mutation scanning and genotyping in the same reaction. Scanning may be performed by high-resolution amplicon melting (8) in the same reaction and using the same melting curve as Snapback genotyping. Asymmetric PCR for Snapback genotyping results in two species with different melting transitions, an excess single strand in a hairpin conformation and a double stranded PCR product, preferably with each species melting at a different temperature. Illustratively, the Snapback hairpin will melt at low temperature, and the full-length amplicon will melt at high temperature. The hairpin provides targeted genotyping for common variants, while the full-length amplicon allows scanning for any sequence variant within the PCR product. Similarly, symmetric PCR using two Snapback primers may be used to scan and to genotype two known polymorphisms in one reaction. In a well-characterized gene with precise amplicon melting, it is believed that Snapback genotyping typically can eliminate at least 90% and perhaps as much as 99% of the need for sequencing in the analysis of complex genetic disease.

Combined scanning and genotyping with Snapback primers is attractive because only PCR reagents and a dsDNA dye are needed. No expensive modified oligonucleotides, separations, purifications or reagent addition steps are necessary. Closed-tube analysis eliminates the risk of PCR contamination. Furthermore, Snapback primer annealing is rapid and compatible with the fastest PCR protocols.

SUMMARY OF THE INVENTION

Accordingly, Snapback primers in various configurations are described herein.

In one aspect of the present invention a method for nucleic acid analysis is provided, the method comprising the steps of mixing a target nucleic acid with a first primer and a second primer to form a mixture, the primers configured for amplifying the target nucleic acid, wherein the first primer comprises a probe element specific for a locus of the target nucleic acid and a template-specific primer region, wherein the probe element is 5' of the template-specific primer region, amplifying the target nucleic acid to generate an amplicon, allowing the probe element to hybridize to the locus to form a hairpin, generating a melting curve for the probe element by measuring fluorescence from a dsDNA binding dye as the mixture is heated, wherein the dye is not covalently bound to the first primer, and analyzing the shape of the melting curve. A number of variations on this method are provided herein.

In a second aspect of the present invention methods are provided for simultaneous scanning and genotyping of a target nucleic acid, the methods comprising the steps of mixing the target nucleic acid with a first primer and a second primer to form a mixture, the primers configured for amplifying the target nucleic acid, wherein the first primer comprises a probe element specific for a locus of the target nucleic acid and a template-specific primer region, wherein the probe element is 5' of the template-specific primer region, amplifying the target nucleic acid to generate an amplicon, generating a melting curve for the amplicon by measuring fluorescence from a dsDNA binding dye as the mixture is heated, adjusting the mixture to favor hairpin formation by the probe element binding intramolecularly to the target nucleic acid, and generating a melting curve for the probe element by measuring fluorescence from the dsDNA binding dye as the mixture is heated.

In a third aspect of the present invention, a kit is provided for nucleic acid analysis, the kit comprising a first primer and a second primer, the primers configured for amplifying a target nucleic acid, wherein the first primer comprises a probe element specific for a locus of the target nucleic acid and a template-specific primer region and the probe element is 5' of the template-specific primer region, and a dsDNA binding dye. In one illustrative example, the dsDNA binding dye is a saturation dye. In another illustrative example, the kit further comprises a thermostable polymerase and dNTPs.

Additional features of the present invention will become apparent to those skilled in the art upon consideration of the following detailed description of preferred embodiments exemplifying the best mode of carrying out the invention as presently perceived.

BRIEF DESCRIPTION

FIG. 3 shows SNP genotyping using a saturation dye and unlabeled oligonucleotide probes.

FIG. 4 is a schematic of genotyping using Snapback primers.

Figure 6A:
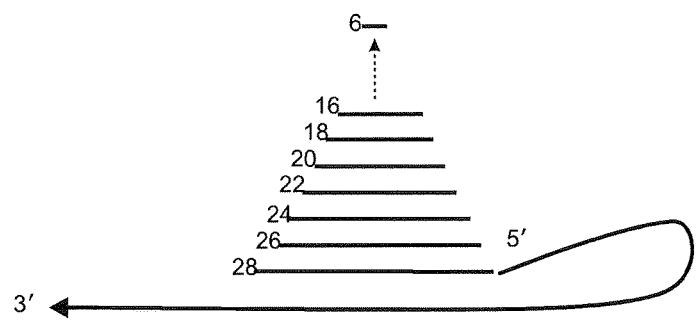

FIG. 6A diagrams Snapback primers having different length probe elements.

Figure 6B:
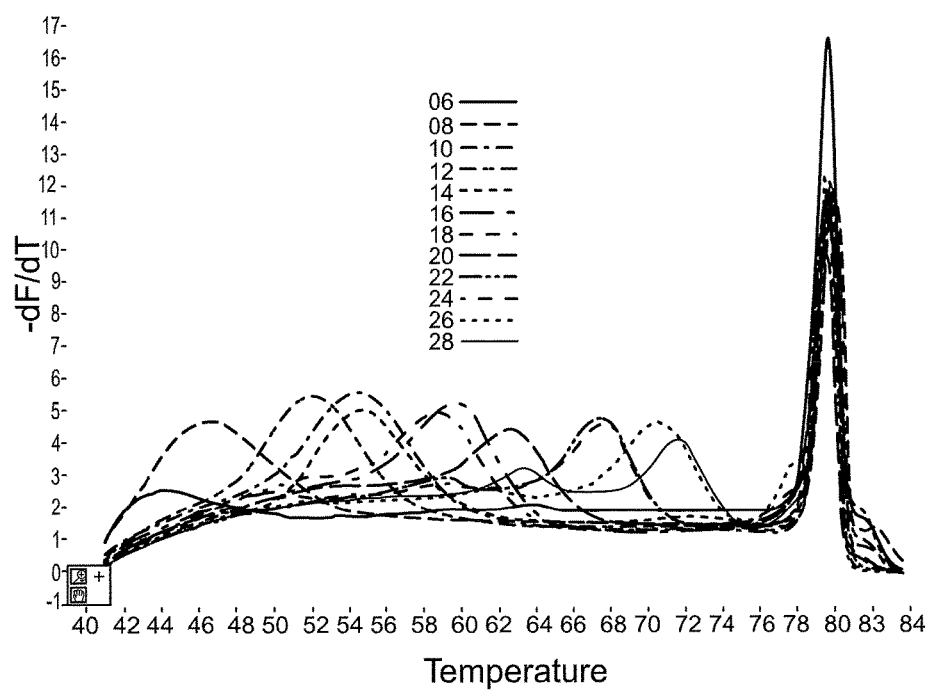

FIG. 6B is a derivative melting plot of amplification products of probe elements of FIG. 6A.

Figure 6C:
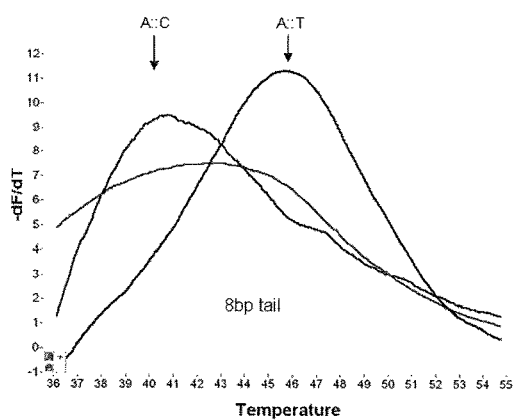
Figure 6D:
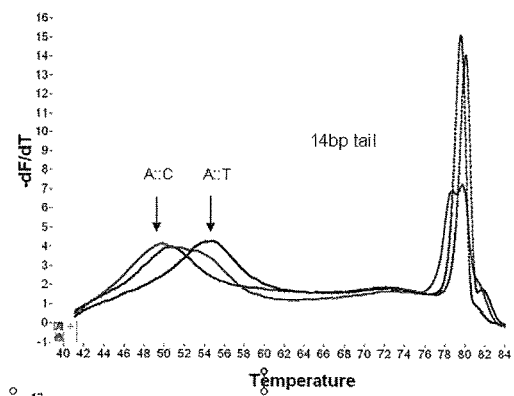
Figure 6E:
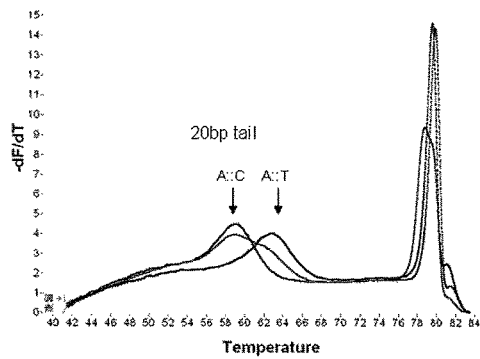
Figure 6F:
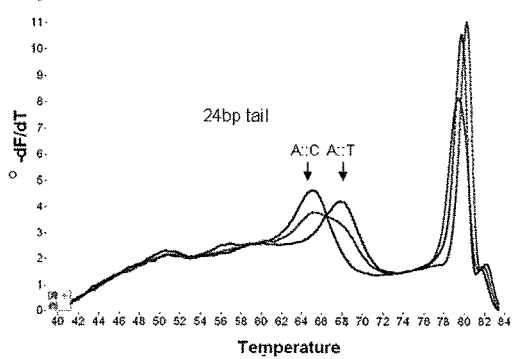

FIGS. 6C-F show derivative melting plots for SNP genotyping using Snapback primers having different probe element lengths: FIG. 6C has an 8 base probe element; FIG. 6D has a 14 base probe element; FIG. 6E has a 20 base element; FIG. 6F has a 24 base element.

Figure 6G:
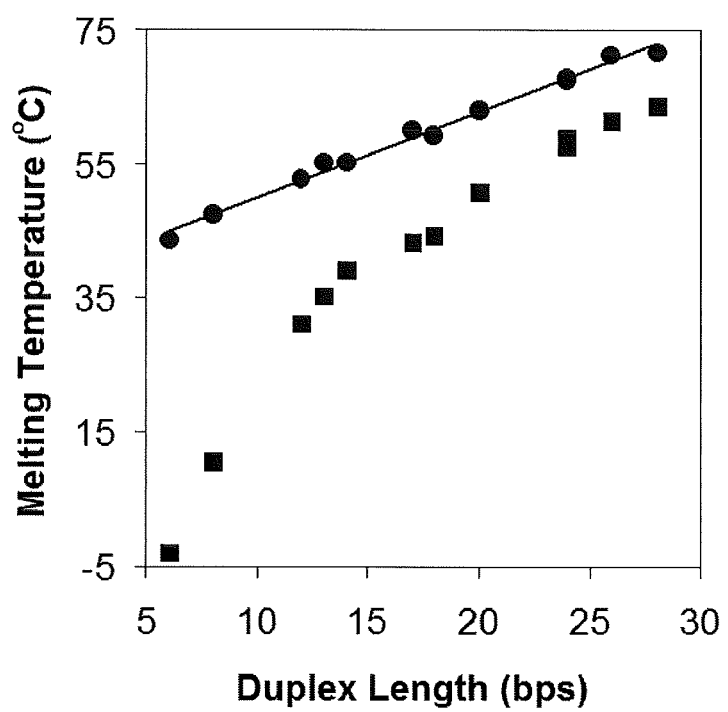

FIG. 6G shows predicted and observed melting temperatures for different hairpin duplex lengths varying from 6 to 28 bps. Base mismatches were not present at the 5'-end of the snapback primers. Predicted melting temperatures (filled squares) were determined by standard nearest neighbor calculations, including dangling ends on both sides, but without consideration of the hairpin loop. After asymmetric PCR and melting, observed Tms (filled circles) were determined as maximum peak heights on negative derivative plots after normalization and exponential background subtraction. The GC % of the hairpin duplex varied from 8.3-32.1%.

FIGS. 7A-B diagram a possible mechanism for inhibition of PCR with Snapback primers, with FIG. 7A showing possible extension from the 3' end of the minor strand, and FIG. 7B showing how a two base mismatch prevents this extension.

FIG. 7C shows normalized derivative melting plots for one hundred clinical samples using a Snapback primer having a two-base mismatch of the type diagrammed in FIG. 7B. Genotypes were homozygous wild type (black), heterozygous (light grey), and homozygous mutant (dark grey).

Figure 8A:
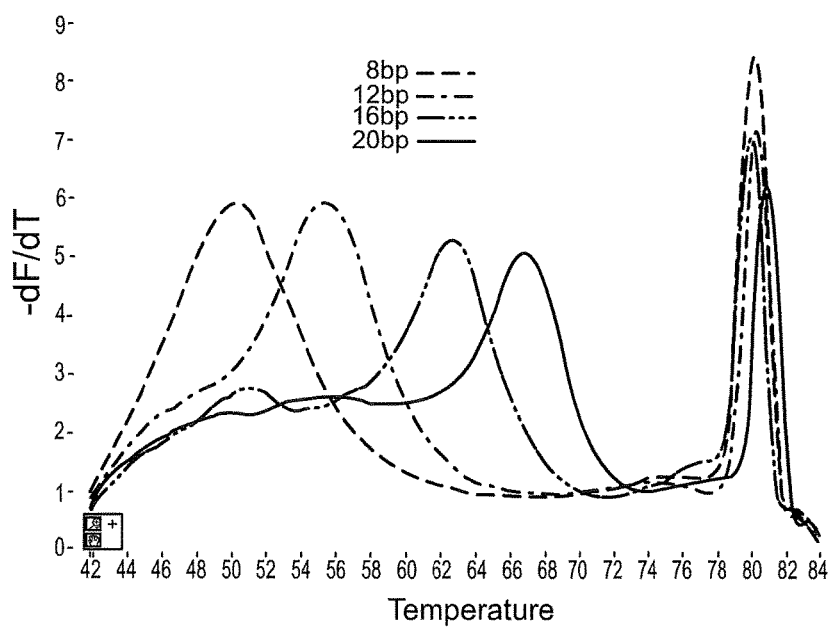

FIG. 8A shows derivative melting plots of 8, 12, 16, and 20 base probe elements in Snapback primers having a two base mismatch to prevent extension from the hairpin.

Figure 8B:
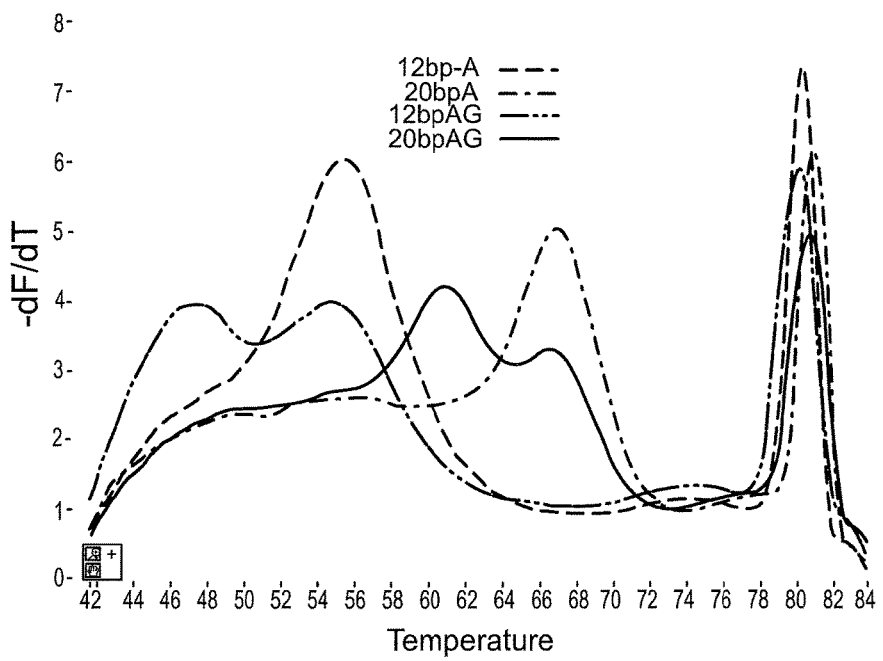

FIG. 8B shows derivative melting plots of 12 and 20 base probe elements after asymmetric amplification with homozygous and matched heterozygous templates.

Figure 9A:
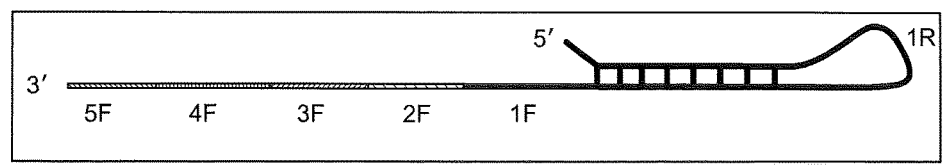

FIG. 9A diagrams Snapback amplicons of varying lengths, wherein the amplicon lengths are: 1=120 bp, 2=180 bp, 3=221 bp, 4=271 bp and 5=321 bp.

Figure 9B:
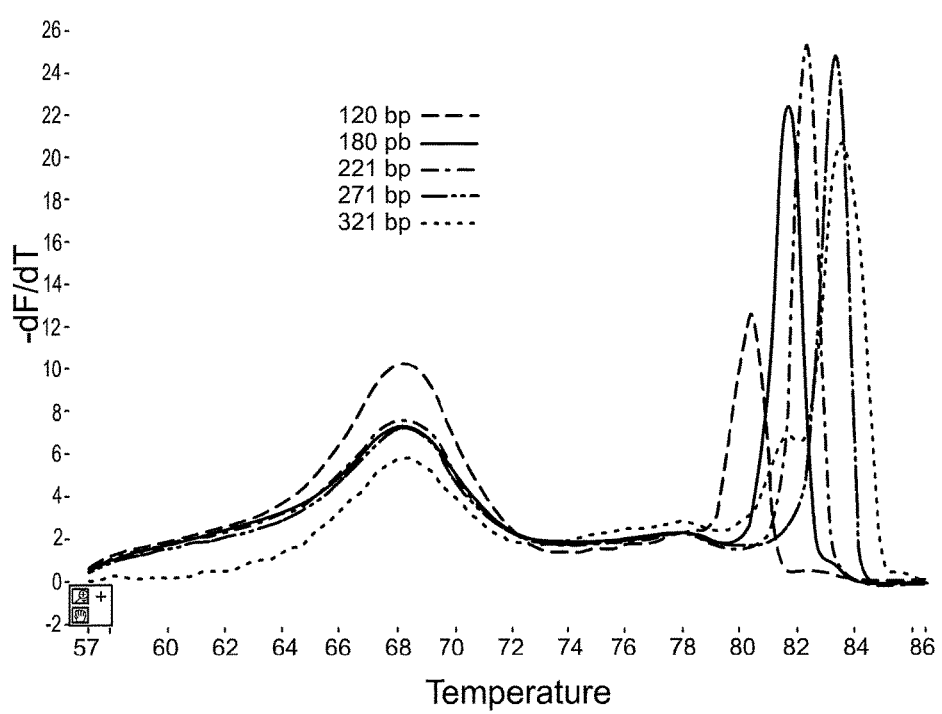

FIG. 9B shows derivative melting plots of the amplicons of FIG. 9A, black (120 bp), red (180 bp), blue (221 bp), green (271 bp), and yellow (321 bp).

Figure 10A:
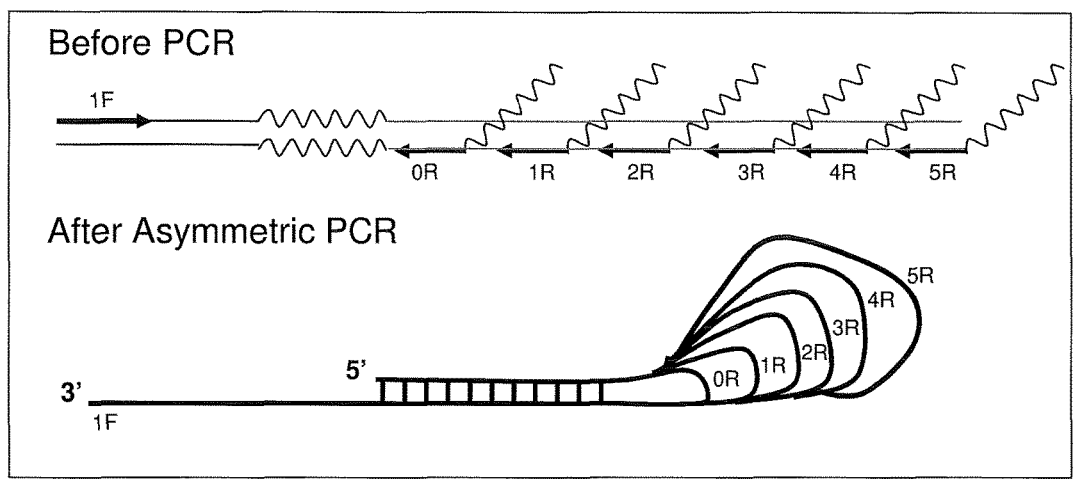

FIG. 10A diagrams Snapback amplicons having various loop sizes. The loop lengths are: 0R=17 bases, 1R=34 bases, 2R=88 bases, 3R=135 bases, 4R=177 bases, and 5R=236 bases.

Figure 10B:
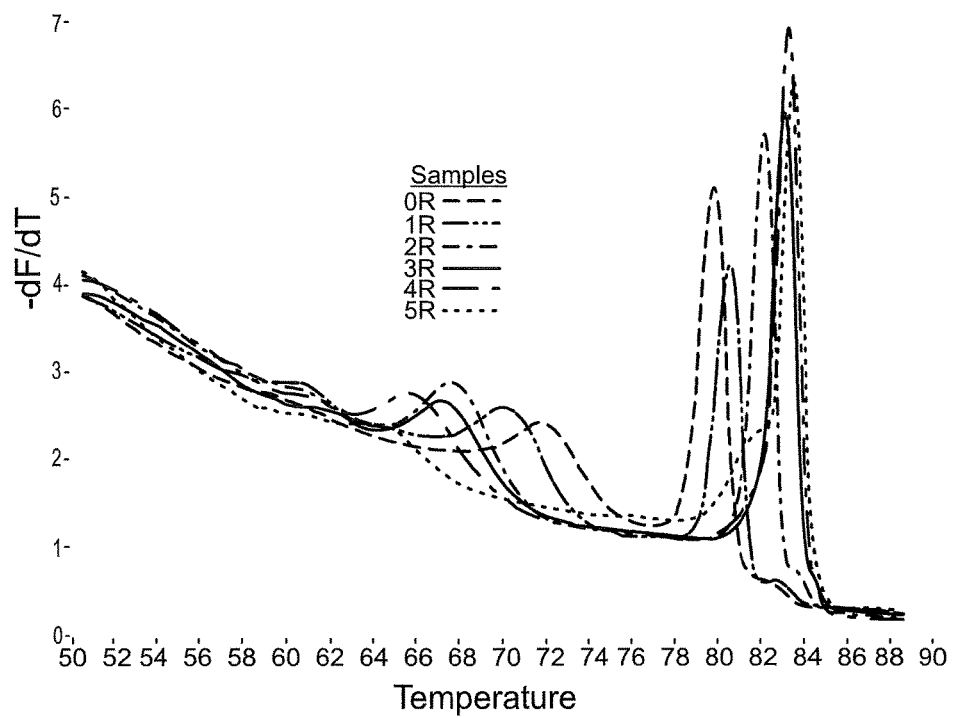

FIG. 10B shows derivative melting plots of the amplicons of FIG. 10A. Exponential background subtraction was not performed, explaining the downward slope of the derivative curve.

Figure 11A:
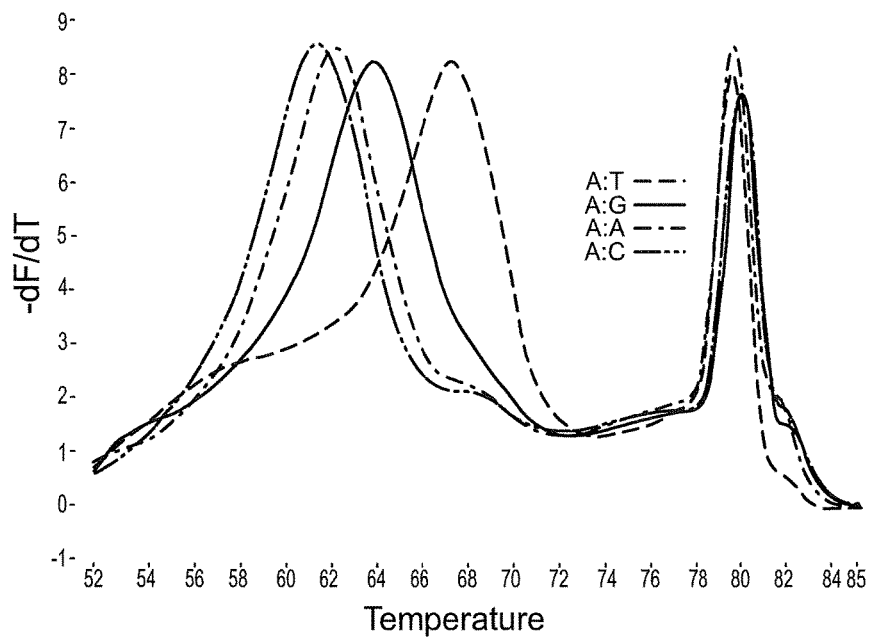

FIG. 11A shows derivative melting plots wherein a Snapback primer was used to amplify four different homozygous templates, each varying solely with a different base at the variable position.

Figure 11B:
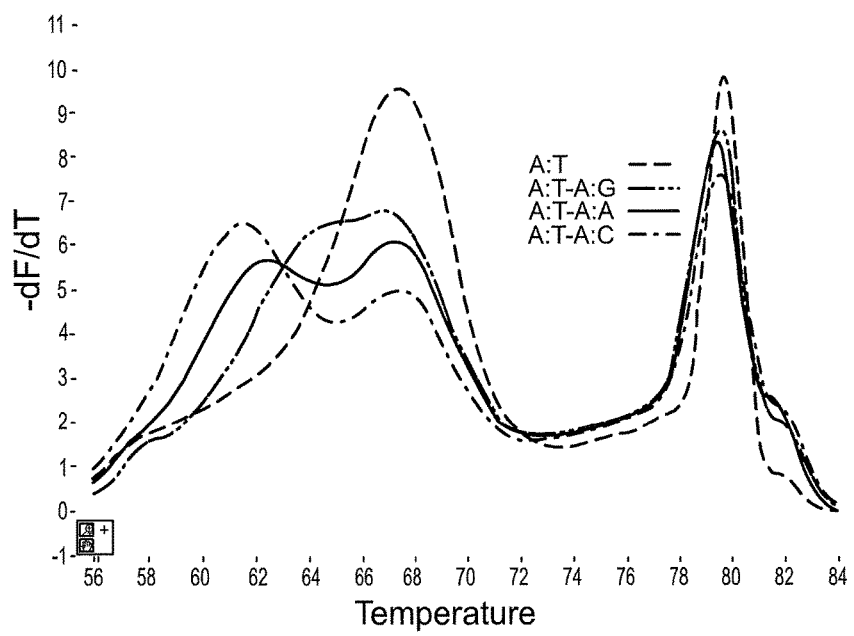

FIG. 11B shows derivative melting plots wherein a Snapback primer was used to amplify one matched homozygous template, and three different heterozygous templates each sharing one matched allele.

Figure 11C:
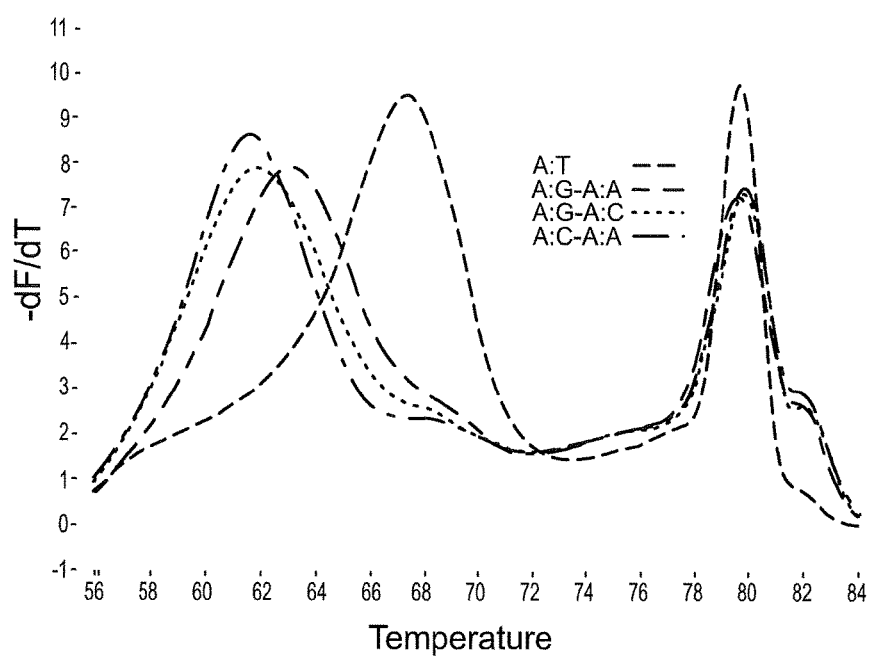

FIG. 11C shows derivative melting plots wherein a Snapback primer was used to amplify one matched homozygous template, and three different heterozygous templates with both alleles mismatched to the probe element.

Figure 12A:
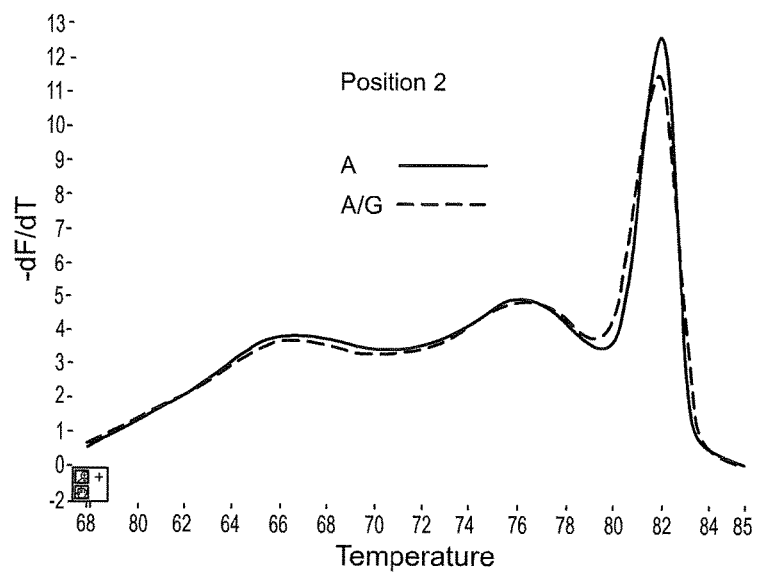
Figure 12B:
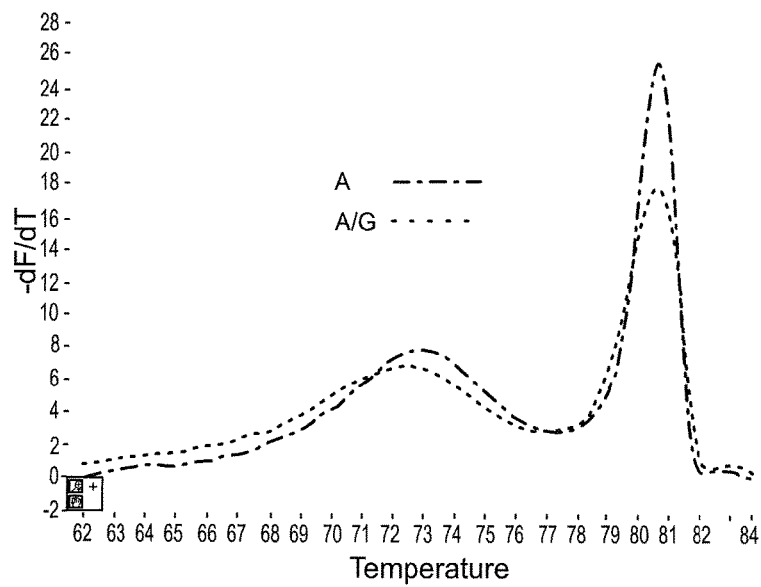

FIGS. 12A-B show derivative melting plots wherein the Snapback primer has a mismatch near the ends of a 22-base probe element. FIG. 12A demonstrates a mismatch at position 2, while the FIG. 12B has a mismatch at position 20.

Figures 12C, 12D:
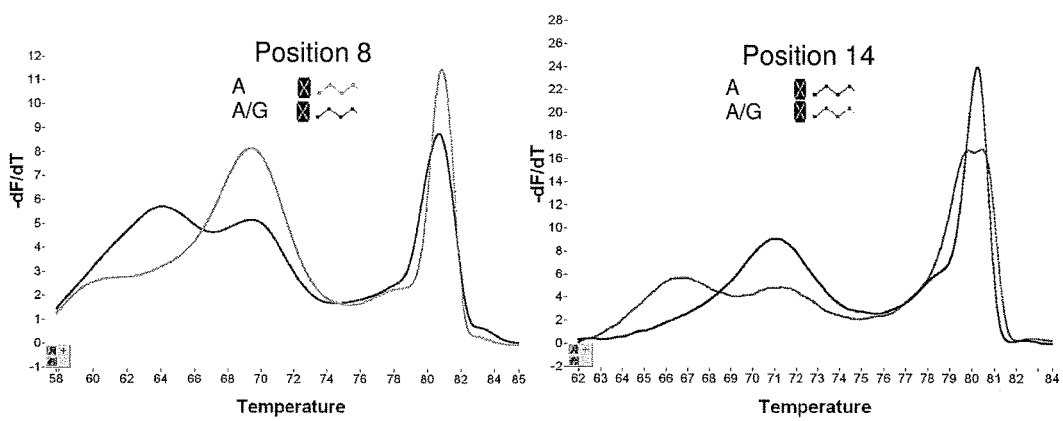

FIGS. 12C-D show derivative melting plots wherein the Snapback primer has a mismatch near the middle of a 22-base probe element. FIG. 12C has a mismatch at position 8, while FIG. 12D has a mismatch at position 14.

Figure 13:
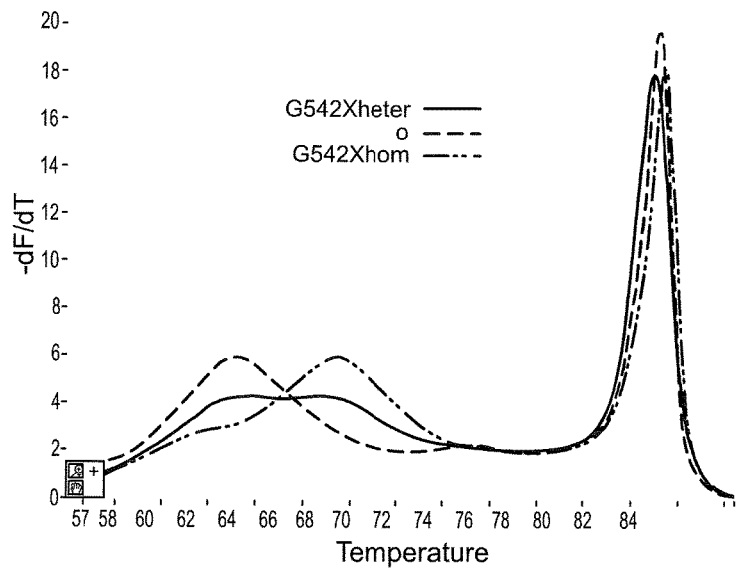

FIG. 13 shows a derivative melting plot of the cystic fibrosis G542x mutation using a Snapback primer. Genotypes shown are homozygous wild type (blue), heterozygous (black), and homozygous mutant (red).

Figures 14A, 14B:
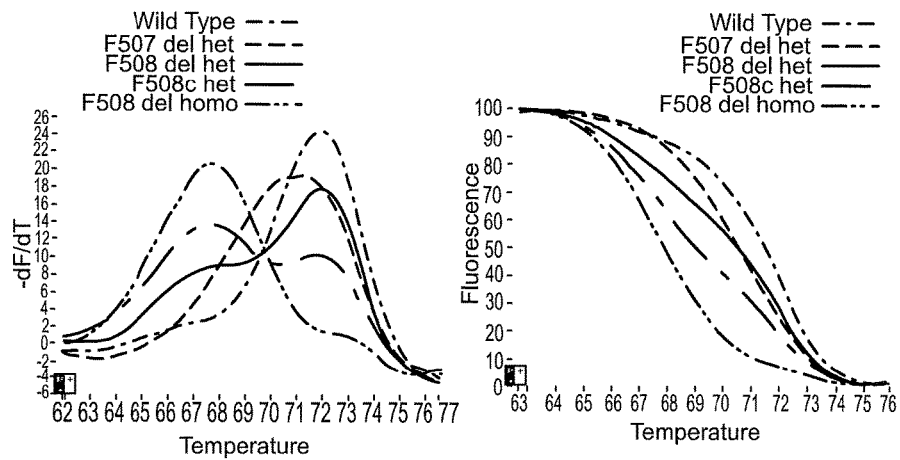

FIGS. 14A-B show derivative plots (FIG. 14A) and normalized melting curves (FIG. 14B) of the probe element of a Snapback primer interrogating the F507-F508 region of CFTR exon 10: wild type (yellow), F507del het (black), F508del het (blue), F508C het (red) and F508del homo (green).

Figure 15:
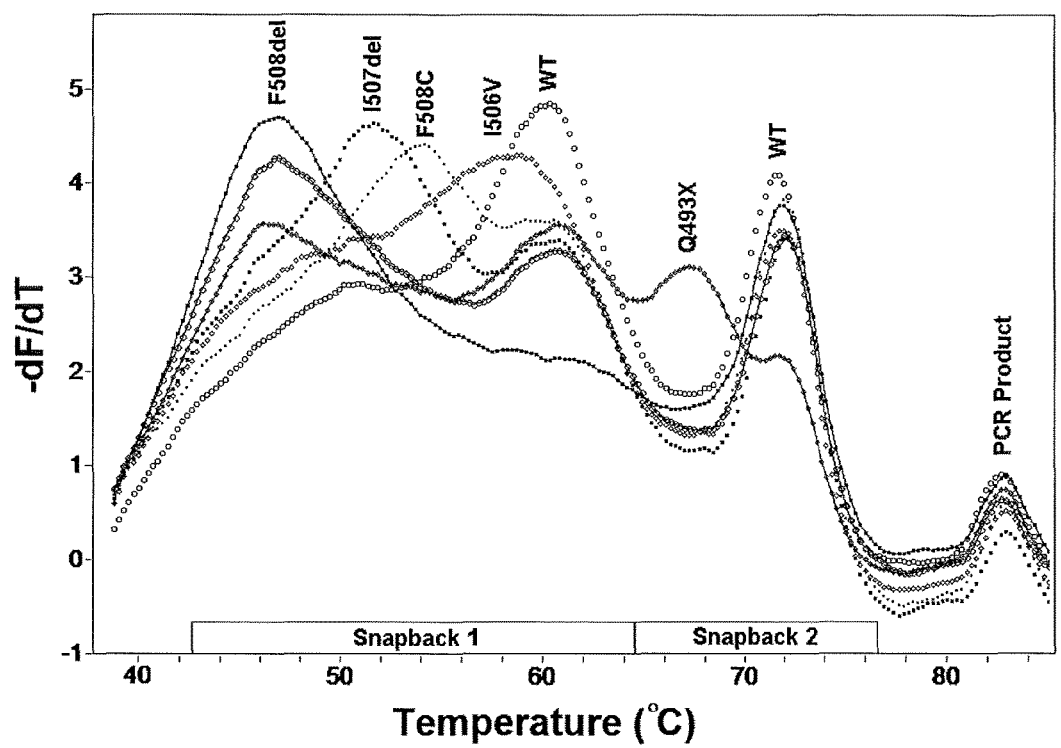

FIG. 15 shows a derivative plot of multi-locus genotyping with bilateral Snapback primers interrogating CFTR exon 10: wild type (circles), compound F508del/Q493X heterozygote (connected small diamonds), I506V heterozygote (small diamonds), F508C heterozygote (small squares), I507del heterozygote (large squares), F508del heterozygote (connected large diamonds), and F508del homozygote (connected squares).

FIG. 16 shows a derivative plot of resonance energy transfer from LCGreen Plus to LCRed640 using a 5'-LCRed640-labeled Snapback primer (red trace melting at 72° C.). In comparison, the melting curve from a non-attached LCRed640 labeled probe is shown in blue with a melting transition of 63° C.

FIG. 17 is a schematic of genotyping and scanning using Snapback primers.

Figure 18A:
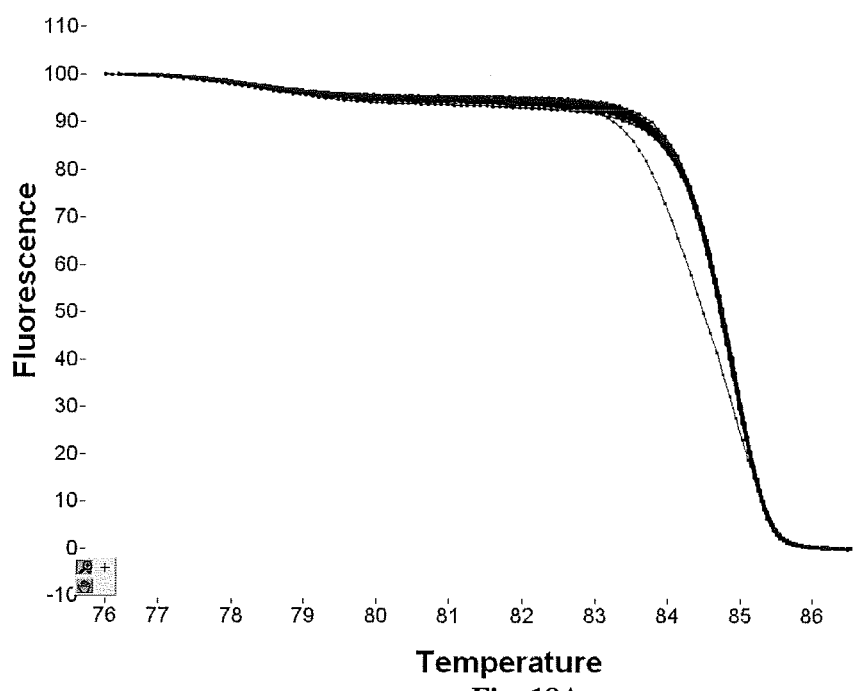
Figure 18B:
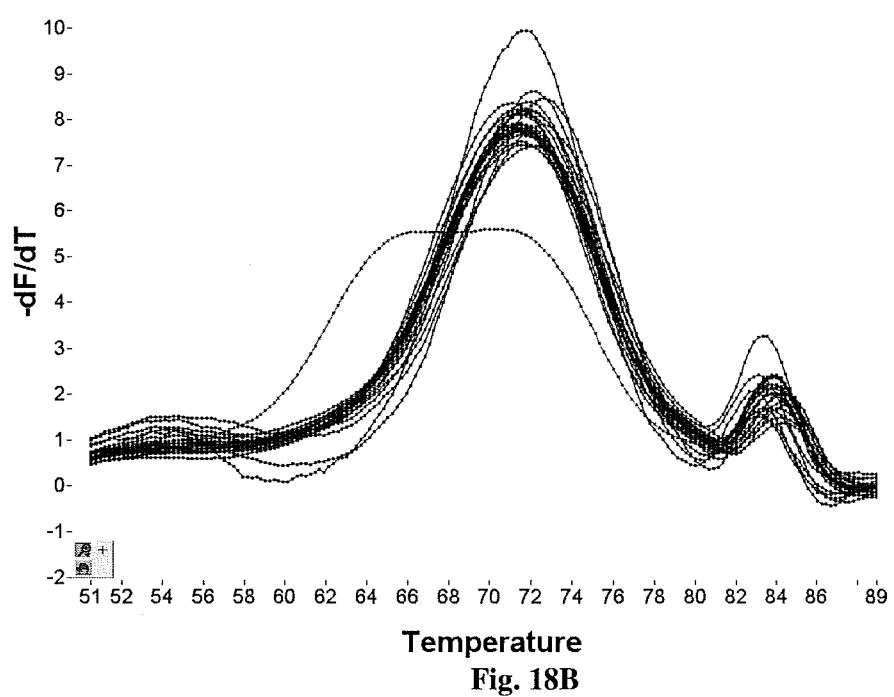

FIGS. 18A-B show simultaneous mutation scanning and genotyping of the CFTR exon 4 using symmetric PCR and one snapback primer. FIG. 18A shows a melting curve of the full length amplicon before dilution with water, while FIG. 18B shows a derivative curve following 10× dilution with water. After dilution, the samples were denatured by heat and cooled prior to melting: wild-type (black) and R117H heterozygote (red).

DETAILED DESCRIPTION

SYBR® Green I (Invitrogen Corp, Carlsbad, Calif.) is a dye extensively used for melting analysis, as it shows a large change in fluorescence during PCR (10, 15). SYBR® Green I was first used in melting analysis to distinguish different PCR products that differed in Tm by 2° C. or more (21). Subsequently, SYBR® Green I was used to identify deletions (16), genotype dinucleotide repeats (17), and identify various sequence alterations (18-21). However, the Tm difference between genotypes can be small and may challenge the resolution of current instruments. Indeed, it has been suggested that SYBR® Green I, "should not be used for routine genotyping applications" (22). Melting curve genotyping with commonly used double-strand-specific DNA dyes can result in an increased Tm with broadening of the melting transition (23), and compression of the Tm difference between genotypes. These factors lower the potential of SYBR® Green I for genotype discrimination.

Heterozygous DNA is made up of four different single strands that can create two homoduplex and two heteroduplex products when denatured and cooled. Theoretically, all four products have different Tms and the melting curve should be a composite of all four double-stranded to single-stranded transitions. However, double-strand-specific DNA dyes may redistribute during melting (24), causing release of the dye from low melting heteroduplexes and redistribution to higher melting homoduplexes. Because SYBR® Green I is not saturating at concentrations compatible with PCR (10), such redistribution is plausible and consistent with the absence of an observed heteroduplex transition.

Recently, LCGreen® I and LCGreen® Plus (Idaho Technology, Inc., Salt Lake City, Utah) and various other saturation dyes have been developed for high resolution applications, including for genotyping and scanning (see co-pending U.S. patent application Ser. Nos. 10/531,966, 10/827,890, 11/485,851, 11/931,174, herein incorporated by reference in their entireties). When only one PCR product is amplified and the sequence is homozygous, only homoduplexes are formed. With saturation dyes, Tm differences between different homoduplex genotypes are not compressed, and clear differentiation between genotypes is possible, even for SNPs. Such saturation dyes can also be used to identify and distinguish multiple products present in a reaction, illustratively homoduplexes generated from amplification of multiple loci or multiple targets that are homozygous. In contrast, most of the time only a few products can be observed with SYBR® Green I, presumably due to dye redistribution.

When one or more heterozygous targets are amplified, heteroduplex products are readily observable with saturation dyes. The ability to detect and identify heteroduplexes is particularly useful for detecting heterozygous genotypes as well as for scanning unknown mutations. In many circumstances, this is not possible with conventional dsDNA dyes used in real-time PCR, such as SYBR® Green I, SYBR® Gold, and ethidium bromide, where heteroduplex products are generally not observable.

With saturation dyes, it is possible to distinguish all single base heterozygotes from homozygotes. In the detection of heterozygotes, the absolute melting temperature and the influence of DNA concentration are not as important as with methods involving differentiation between homozygous genotypes. Heteroduplexes affect the shape of the melting curve, particularly at the "early," low temperature portion of the transition. Different melting curves can be temperature matched by translating the X-axis to superimpose the "late," high temperature portion of the transition. The presence or absence of heteroduplexes can then be inferred with greater accuracy.

Unlabeled oligonucleotides can be used in combination with saturation dyes for genotyping by closed-tube melting analysis (11). Illustratively, the product strand complementary to the unlabeled probe is overproduced by asymmetric PCR, illustratively with the complementary primer in 5-10 fold excess. The unlabeled probe may be blocked at the 3-end to prevent extension, but no other modifications are needed. FIG. 3 shows a typical result of unlabeled probe genotyping from genomic DNA. A segment carrying the cystic fibrosis SNP G542x mutation was amplified in the presence of a 28-mer unlabeled probe (11). All three genotypes are shown (homozygous wild type—solid black line, heterozygous—red line, and homozygous mutant—dashed line) using probes matched to either the wild type (top) or mutant (bottom). Using an unlabeled probe, one can genotype the region under the probe, as shown in FIG. 3, and one can use the melting curve of the entire amplicon, which will generally have a higher melting transition, to scan for mutations elsewhere in the amplicon.

However, it is usually desirable to block the 3'-end of unlabeled probes, to prevent extension. The blocker is an added expense. Additionally, unlabeled probe genotyping requires three oligonucleotides: two primers and an additional unlabeled probe. Furthermore, unlabeled probes give the best signal when they are relatively long, usually 25-35 bases (11). Finally, the intermolecular hybridization required with unlabeled probes can be blocked by secondary structure of the target, because intermolecular hybridization is usually slower than intramolecular hybridization of secondary structure.

Snapback primers according to the present disclosure address many of these issues. First, only two oligonucleotides are necessary, illustratively a standard primer and a primer with a short tail as an integrated probe element. Next, no 3'-end blocking is necessary because the probe element is a part of the 5'-end of the primer, and extension of the primer is desired. Finally, Snapback primer hybridization is intramolecular, so hybridization is rapid and internal structure is less of a concern. When a saturation dye is used, the saturation dye may be present during amplification in sufficient concentration to detect heteroduplexes upon amplicon melting. Thus, the combination of Snapback primers and saturation dyes provide a closed-tube solution nucleic acid analysis. However, while the examples herein use saturation dyes, it is understood that Snapback primers may be used with other dyes, particularly wherein high resolution is not necessary or where dye addition subsequent to amplification is not a problem.

An illustrative Snapback genotyping protocol is diagrammed in FIG. 4. The Snapback primer is shown on the left, as it has a tail 8 that does not hybridize to the target nucleic acid 20. The standard primer 12 is shown on the right. The nucleic acid is amplified, illustratively by asymmetric PCR, producing more of the strand 14 made from extension of Snapback primer 10 than of the complementary strand 16. The amplification product is then cooled, producing a mixture of intramolecular hairpin products 30 from the Snapback primer 10, along with some double stranded full-length amplicon 40. A derivative melt of this amplification mixture produces low temperature peaks representing melting of the hairpin structure 35, and high temperature peaks representing melting of the full-length amplicon 40.

While PCR is the amplification method used in the examples herein, it is understood that any amplification method that incorporates a primer may be suitable. Such suitable procedures include polymerase chain reaction (PCR); strand displacement amplification (SDA); nucleic acid sequence-based amplification (NASBA); cascade rolling circle amplification (CRCA), loop-mediated isothermal amplification of DNA (LAMP); isothermal and chimeric primer-initiated amplification of nucleic acids (ICAN); target based-helicase dependant amplification (HDA); transcription-mediated amplification (TMA), and the like. Therefore, when the term PCR is used, it should be understood to include other alternative amplification methods.

Further, while reference is made to post-amplification genotyping, it is understood that the primers described herein may be used for detection and/or quantification. The Snapback primer serves both as a primer and as a probe for such methods, as are known in the art.

EXAMPLE 1

Genotyping with a Snapback Primer after Symmetric PCR

An engineered plasmid template of M13 sequence with 40% GC content was used as template (25). Otherwise identical plasmids with either an A, C, G, or T at one position were available for study. Both the "A" template and the "C" template were studied, as well as a "A/C" heterozygote that was formed by mixing equal amounts of the "A" and "C" templates. The concentration of each plasmid was determined by absorbance at 260 nm ($A_{260}$), assuming an $A_{260}$ of 1.0 is 50 µg/mL. The M13 primers used are forward 5'-AATCGTCATAAATATTCATTGAATCCCCtcat-tctcgttttctgaactg-3' (SEQ ID NO. 1, with the tail shown in caps and the variable position on the template after the Snapback hairpin is formed shown in bold), and reverse 5'-atgtttagactggatagcgt-3' (SEQ ID NO. 2), which form a PCR product of about 130 bps.

PCR was performed in 10-ul reaction volumes with 50 mM Tris (pH 8.3), 500 µg/ml bovine serum albumin, 3 mM $MCl_2$, 200 µM of each deoxynuleotide triphosphate, 0.4 U of Klen Taq polymerase (AB Peptides), 0.5X LCGreen® Plus (Idaho Technology), 0.5 µM primers and $10^6$ copies of the "A" plasmid or an equivalent concentration of a 1:1 mixture of the "A" and "C" plasmids. PCR was performed in a LightCycler® (Roche) for 35 cycles with denaturation at 95° C. (0 s hold), annealing at 50° C. (0 s hold), a 2° C./s ramp to the extension temperature at 72° C. and an 8 s hold at 72° C. After PCR, the capillary samples were denatured at 94° C. (0 s hold) and cooled to 40° C. All transition rates between temperatures were programmed at 20° C./s unless otherwise stated. The samples were removed from the LightCycler, placed in the high-resolution melting instrument HR-1™ (Idaho Technology), and melted from 50° C. to 87° C. at a 0.3° C./s ramp. Usually, exponential background was subtracted from the melting curves, illustratively as described in PCT/US2006/036605, herein incorporated by reference in its entirety, the curves are normalized and usually displayed as derivative plots. The resultant derivative melting curves are shown in FIG. 5A.

Figure 1:
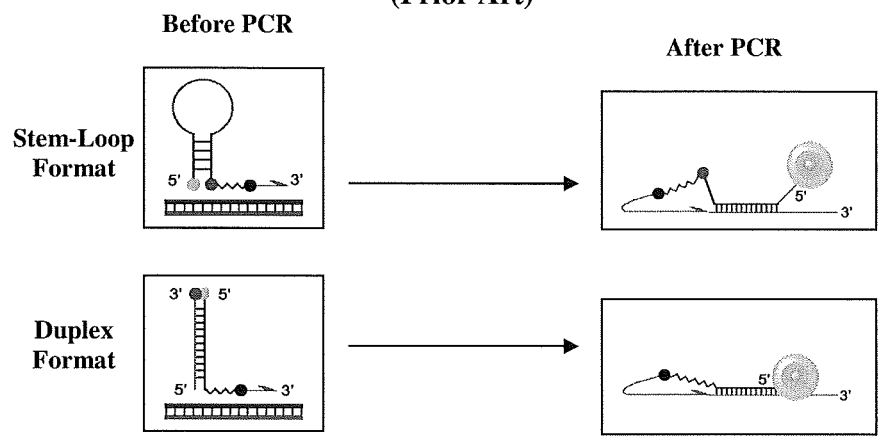
FIG. 1 shows a schematic of the action of Scorpion® primers. The black circle is the blocker, the red circle is the quencher, the small green circle is the quenched fluorophore, and the large green circle is the unquenched fluorophore.
Figure 2:
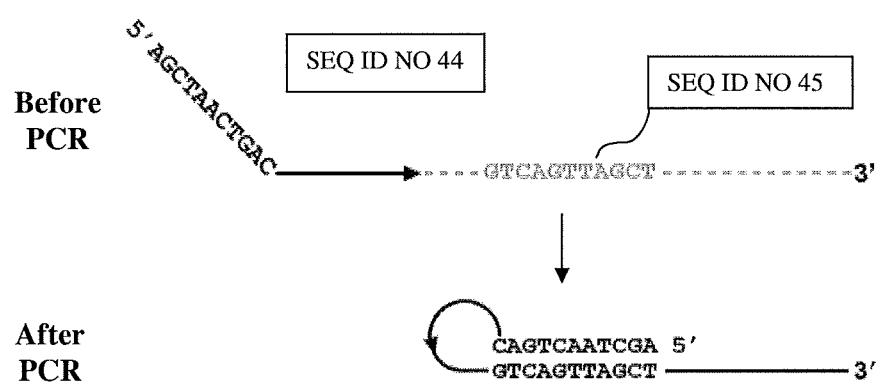
FIG. 2 shows the intramolecular hybridization of a Snapback primer.
Figure 5A:
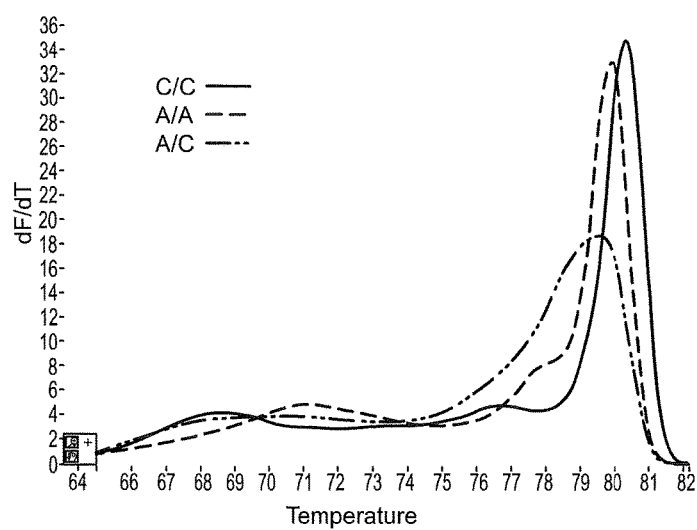
FIG. 5A shows genotyping using a Snapback primer following symmetric PCR. The genotypes shown are C/C (blue), A/A (black) and A/C (red).

FIG. 5A shows derivative melting curve plots for all genotypes of an A/C SNP. Both amplicon (78-82° C.) and snapback probe (66-73° C.) melting transitions are apparent. Considering first the amplicon region, the peak of the C homozygote is at a higher temperature than the A homozygote, as expected. Furthermore, the AC heterozygote shows a broad transition at lower temperatures because of the influence of heteroduplexes (12). Melting of the probe element of the Snapback primer depends on the genotype. The perfectly matched A template melts at the highest temperature (71° C.), the mismatched C template melts at 68° C., and the heterozygote shows melting peaks at both temperatures. Although the signal intensity is low, the ability to genotype by observing the melting of the probe element of the Snapback primer is clearly evident.

EXAMPLE 2

Snapback Primer Genotyping with an Extension Blocker Using Symmetric PCR

To increase Snapback primer loop formation and the height of the Snapback genotyping peaks (low temperature peaks) on derivative plots, an extension blocker was incorporated between the template-specific primer and the probe element of the Snapback primer. Shown as an "X" in the forward primer, the blocker used was an abasic tetrahydrofuran derivative incorporated as the dSpacer CE phosphoramidite available from Glen Research (cat. no. 10-1914-90). Ten contiguous dSpacer units were incorporated in order to ensure blockage of the polymerase. The primers used are forward 5'-AATCGTCATAAATATTCATTGAATCCCC(X)$_{10}$tcattctcgttttctgaactg-3' (SEQ ID NO. 3, with tail shown in caps and variable position on the template after the Snapback hairpin is formed shown in bold), and reverse 5'-atgtttagactggatagcgt-3' (SEQ ID NO. 4).

Figure 5B:
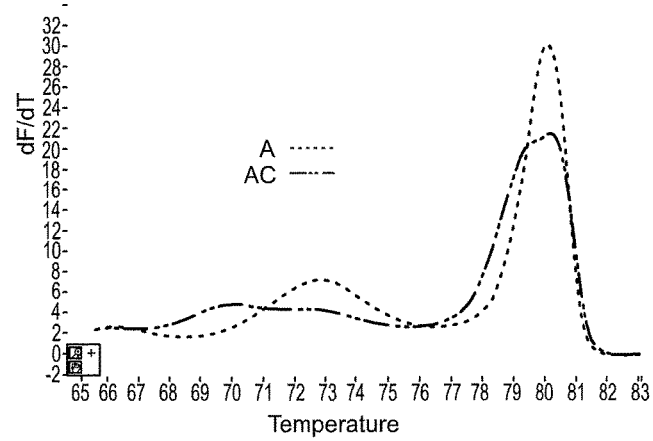
FIG. 5B shows genotyping using a Snapback primer with an extension blocker.

Both the "A" template and the "A/C" heterozygote of Example 1 were studied. PCR and melting were performed as outlined in Example 1. FIG. 5B shows derivative melting curve plots for both the A and A/C genotypes. Both amplicon (78-82° C.) and snapback probe (68-75° C.) melting transitions are apparent. Considering the amplicon region, the AC heterozygote has a broad transition at lower temperatures compared to the homozygote. Melting of the probe element of the Snapback primer depends on the genotype. The perfectly matched A template melts in one transition at a high temperature (73° C.), while the heterozygote transition is bimodal. The probe element signal increased in relative intensity compared to Example 1.

One advantage of using symmetric PCR for Snapback primer genotyping is that two Snapback primers can be used (one on each end) to interrogate two different loci within the PCR product. Each tail is made complementary to one locus and the probe elements may be varied in length and/or GC content to separate the Tms of the alleles of the two probe elements. Another illustrative way to interrogate distant loci (separated by such a distance that one probe element would be inconvenient), is to use only one Snapback primer with a single probe element, but divide the probe element into two or more segments, each segment complementary to one of the loci. The template DNA forms loops between the loci and haplotyping is possible (13). Alternatively, one Snapback primer and one unlabeled probe (11) can be used, illustratively with asymmetric PCR. Another option is to mix several Snapback primers together, each with the same template-specific primer region but different probe elements that target different loci.

EXAMPLE 3

Effect of the Length of the Probe Element on the Signal of Snapback Primers after Asymmetric PCR Different probe element lengths were investigated using asymmetric PCR. The M13 primers used are shown in Table 1, wherein upper case indicates the probe element tail, lower case defines the template-specific primer region, and the bold face base indicates the variable position on the template after the Snapback hairpin has formed.

TABLE 1

| Name | |
|---|---|
| | Limiting Forward Primer (0.05 µM) |
| 1F | tcattctcgttttctgaactg (SEQ ID NO: 5) |
| | Snapback Reverse Primer (0.5 µM) |
| 1R6tail | GAATATatgtttatagactggatagcgt (SEQ ID NO: 6) |
| 1R8tail | TGAATATTatgtttatagactggatagcgt (SEQ ID NO: 7) |
| 1R10tail | ATGAATATTTatgtttagactggatagcgt (SEQ ID NO: 8) |
| 1R12tail | AATGAATATTTAatgtttagactggatagcgt (SEQ ID NO: 9) |
| 1R14tail | CAATGAATATTTATatgtttagactggatagcgt (SEQ ID NO: 10) |
| 1R16tail | TCAATGAATATTTATGatgtttagactggatagcgt (SEQ ID NO: 11) |
| 1R18tail | TTCAATGAATATTTATGAatgtttagactggatagcgt (SEQ ID NO: 12) |

TABLE 1-continued

| Name | |
|---|---|
| 1R20tail | ATTCAATGAATATTTATGACatgtttagactggatagcgt (SEQ ID NO: 13) |
| 1R22tail | GATTCAATGAATATTTATGACGatgtttagactggatagcgt (SEQ ID NO: 14) |
| 1R24tail | GGATTCAATGAATATTTATGACGAatgtttagactggatagcgt (SEQ ID NO: 15) |
| 1R26tail | GGGATTCAATGAATATTTATGACGATatgtttagactggatagcgt (SEQ ID NO: 16) |

PCR and melting were performed as in Example 1, except that 45 cycles were used, the limiting forward primer concentration was 0.05 μM and the Snapback reverse primer concentration was 0.5 μM. While a 10:1 ratio was used, it is understood that other primer ratios may be suitable, as are known in the art, for example from 2:1 to 20:1, or even as high as 100:1. To determine the effect of probe element length on the Snapback primer method, probe regions between 6 and 28 bases long were tested (FIG. 6A). The resultant melting curves are shown in FIG. 6B. The melting curves of Snapback primers are visible even with a probe region as small as 6 bases long. The ability to see duplex melting transitions as small as six base pairs was surprising. Compared to unlabeled probes of the same sequence (11), the melting transitions appear to be stabilized by 5-10° C. or more. A comparison of melting using an amplicon generated from the 1F forward primer and the 1R26tail Snapback reverse primer vs. melting using an unlabeled probe having the same sequence as the 1R26tail probe element confirmed about a 10° C. stabilization due to the intramolecular hybridization. The stabilization has been shown to be even greater for Snapback primers with shorter probe elements that result in short hairpin duplexes. For example, the Tm of a Snapback duplex of 6 bps was 40° C. greater, and the 8 bp Snapback duplex was 35° C. greater, than predicted by nearest neighbor analysis. The linear relationship between duplex length and Tm shown in FIG. 6G suggests that melting temperatures can be accurately predicted by the duplex length.

The Tm of the hairpin duplex can also be adjusted by purposely introducing mismatches, base analogs, or stabilizing moieties into the probe element of the snapback primer. For example, bases that result in mismatches to the template can be used to decrease the overall Tm of the hairpin duplex. G:T mismatches (obtained by replacing at C with a T in the probe element) are particularly attractive because they reduce the hairpin duplex Tm by disrupting a stable C:G pair, but the G:T pair is stable enough that it does not significantly decrease fluorescence from the saturating dye. Mismatches can also be used to mask sequence variants that are best ignored, such as benign polymorphisms. (26). If greater stabilization of the hairpin duplex is desired, locked nucleic acids can be incorporated into the probe element, or a minor groove binder can be attached to increase the melting temperature.

Probe regions of 8, 14, 20 and 24 bp were selected for SNP genotyping. Heterozygotes were formed by mixing the appropriate plasmids in a 1:1 proportion. Results of SNP typing are shown in FIGS. 6C-F. Genotyping was possible with all Snapback primers, including that with a probe element length as short as 8 bases (FIG. 6C).

EXAMPLE 4

Using a 2-Base Terminal Mismatch to Increase the Probe Element Signal: The Effect of Probe Element Length after Asymmetric PCR Some initial attempts at Snapback genotyping from genomic DNA did not work particularly well. With asymmetric PCR, amplification appeared to be inhibited, with low signals appearing only after many cycles, illustratively 60 cycles or more. Further consideration of the major and minor strands that form provided a possible explanation and solution. In FIG. 7A, both the major and minor strands produced after asymmetric PCR are shown in Snapback conformation. Although the major strand cannot extend from its 5'-end, the minor strand does have a 3'-end that can hybridize and form a polymerase substrate. Extension may occur from this 3'-end, inhibiting primer annealing and preventing major strand formation. One solution to this problem is to mismatch the last two bases at the 5'-end of the Snapback primer so that extension from the minor strand is not possible (FIG. 7B). While two bases are used for the illustrative mismatches, it is understood that a one-base mismatch will inhibit some extension, and more bases can be added to the mismatch, if desired. The mismatch will be carried forward into successive rounds of amplification.

A 2-base mismatch incorporated at the 5'-terminus of the probe element of Snapback primers results in strong probe melting signals. As discussed above, such a mismatch prevents PCR inhibition that may otherwise occur after extension from the 3'-end of the minor strand during PCR. Different probe element lengths with 2-bp terminal mismatches were investigated using asymmetric PCR. The M13 primers used are shown in Table 2, wherein upper case indicates the probe element or tail, lower case defines the template-specific primer region, lower case italics indicates bases that are mismatched to the target, and the bold face base indicates the variable position on the template after the Snapback hairpin has formed.

TABLE 2

| Name | |
|---|---|
| | Limiting Forward Primer (0.05 µM) |
| 1F | tcattctcgttttctgaactg (SEQ ID NO: 5) |
| | Snapback Reverse Primer (0.5 µM) |
| 1R8tailM | ccTGAATATTatgtttagactggatagcgt (SEQ ID NO: 17) |
| 1R12tailM | gtAATGAATATTTAatgtttagactggatagcgt (SEQ ID NO: 18) |
| 1R16tailM | cgTCAATGAATATTTATGatgtttagactggatagcgt (SEQ ID NO: 19) |
| 1R20tailM | tcATTCAATGAATATTTATGACatgtttagactggatagcgt (SEQ ID NO: 20) |

PCR and melting were performed as in Example 3. Probe element lengths of 8, 12, 16 and 20 bases, each with a 2 base terminal mismatch, were investigated. FIG. 8A shows derivative melting profiles after asymmetric PCR using the perfectly matched "A" template. All probe element peaks are large and easily identified. Surprisingly, the area under the 8-base probe element is as large as the longer length probe elements.

The ability to genotype is demonstrated in FIG. 8B, using both "A" and "A/G" (heterozygous) templates. The "A" template forms a perfect match to the probe element, whereas the "G" template forms an A/C mismatch, resulting in a melting peak 6-8° C. lower than the perfect match.

One hundred previously typed clinical samples were PCR amplified on a 384-well plate and melted on a 384-well LightScanner® (Idaho Technology). A Snapback primer with a 16-base probe element and a two-base 5'-end mismatch was used in asymmetric PCR, producing a 169 bp PCR product and a hairpin with a 99-base loop. After normalization and background subtraction of the hairpin duplex region, the curves were displayed on a negative derivative plot and automatically clustered. The probe element has a G:T mismatch to the mutant allele. FIG. 7C shows that the genotypes are readily distinguishable. The genotype of all samples in FIG. 7C agreed with the genotypes that were previously determined by high resolution melting of small amplicons.

EXAMPLE 5

Influence of Amplicon Length on Snapback Primer Signal with a Two Base Mismatch on the Probe Element 5'-End Using Asymmetric PCR A Snapback primer having a two-base terminal mismatch, as in Example 4, was used to study different amplicon lengths. The distance from the snapback primer to the SNP site was kept constant (the secondary structure loop remains the same), while the length of the amplicon was varied. Asymmetric PCR was performed as in Example 3. The M13 primers used are shown in Table 3, wherein upper case indicates the probe element or tail, lower case defines the template-specific primer region, lower case italics indicates bases that are mismatched to the target, and the bold face base indicates the variable position on the template after the Snapback hairpin has formed.

TABLE 3

| Name | |
|---|---|
| | Limiting Forward Primer (0.05 µM) |
| 1F | tcattctcgttttctgaactg (SEQ ID NO: 5) |
| 2F | gcaatccgctttgcttctga (SEQ ID NO: 21) |
| 3F | gatatttgaagtctttcggg (SEQ ID NO: 22) |
| 4F | gttggagtttgcttccggtc (SEQ ID NO: 23) |
| 5F | atgacctcttatcaaaagga (SEQ ID NO: 24) |
| | Snapback Reverse Primer (0.5 µM) |
| 1R22tailM | tcGATTCAATGAATATTTATGACGatgtttagactggatagcgt (SEQ ID NO: 25) |

The experimental design is diagrammed in FIG. 9A. In all cases, the Snapback primer is the same, thus forming the same loop size when the probe element anneals to the amplicon, with the same 2 bp mismatch at the 5' end. However, the amplicon length is varied from 120 bp to 321 bp.

Results are shown in FIG. 9B. The longer the amplicon, the smaller the size of the probe element signal compared to the amplicon signal. That is, shorter amplicons will generally result in stronger relative signals from the probe elements.

EXAMPLE 6

Effect of the Loop Length on the Probe Element Signal

The effect of differing loops lengths was investigated by varying the distance between the Snapback primer and the locus to be interrogated. Asymmetric PCR was performed as in Example 3. The M13 primers used are shown in Table 4, wherein upper case indicates the probe element tail, lower case defines the template-specific primer region, and the bold face base indicates the variable position on the template after the snapback hairpin has formed. In this case, 2 bp 5'-mismatches adjacent to the probe element were not used.

TABLE 4

| Name | |
|---|---|
| | Limiting Forward Primer (0.05 µM) |
| 1F | tcattctcgttttctgaactg (SEQ ID NO: 5) |
| | Snapback Reverse Primer (0.5 µM) |
| 0R24tail | GGATTCAATGAATATTTATGACGAcgtccaatactgcggaa (SEQ ID NO: 26) |
| 1R24tail | GGATTCAATGAATATTTATGACGAatgtttagactggatagcgt (SEQ ID NO: 15) |
| 2R24tail | GGATTCAATGAATATTTATGACGAaaaatagcgagaggcttttgc (SEQ ID NO: 27) |
| 3R24tail | GGATTCAATGAATATTTATGACGAtaagagcaacactatcataa (SEQ ID NO: 28) |
| 4R24tail | GGATTCAATGAATATTTATGACGAaatgcagatacataacgcca (SEQ ID NO: 29) |
| 5R24tail | GGATTCAATGAATATTTATGACGAcaacattattacaggtaga (SEQ ID NO: 30) |

The experimental design is diagrammed in FIG. 10A. The relative positions of the primers before PCR are indicated on top. PCR and melting was performed as in Example 3. The loop conformation of the extended Snapback primer after asymmetric PCR is shown on the bottom of FIG. 10A. The loop size varied from 17-236 bp.

The derivative melting curves of the six different products are shown in FIG. 10B. It is noted that the Tm for the full-length amplicon is directly related to amplicon size. With respect to Snapback probe tail melting in which all probe tails were of the same size, smaller loops resulted in higher melting temperatures, indicating that stabilization of intramolecular hybridization is inversely related to loop size, at least between 17-236 bases. The inverse relationship appears to be logarithmic between 17 and 150 bases, with the Tm inversely proportional to the log of the log size. Steric hindrance may become an issue with loops that are smaller than 17 bases, but this is unlikely to be a concern most cases, since the minimum loop size is generally dictated by the primer size. The signal strength of Snapback primers that form larger loops may be decreased relative to the amplicon signal, as seen in Example 5 and with unlabeled probes (11). For example, the melting curve with a loop of 236 bp (5R) loop length is weak. With this illustrative amplicon, the best signals were obtained with loop sizes between 17 and 177 bases, and it is expected that good signals would be obtained with loops of less than 200 bases. Because stabilization of the probe element and large relative signals are generally preferred, loop sizes between 20 and 50 bases are expected to work well.

EXAMPLE 7

Genotyping all Possible Single Base Variants with One Snapback Primer

A single Snapback primer was used to amplify various plasmid templates to demonstrate that the shape of the probe element melting curve depends on the amplified sequence. Four different M13 plasmids were used as the target, wherein each plasmid differed only at one position with an A, C, G, or T. In this example, to simulate homozygote genotyping, only one matched or mismatched plasmid was used, while to simulate heterozygotes two plasmids mixed in equal proportions were used. Asymmetric PCR was performed as in Example 3. The M13 primers used are 1F tcattctcgttttctgaactg (SEQ ID NO:5) and 1R22Tmis10 tcAT-TCAATGAATATTTATGACGAatgtttagactggatagcgt (SEQ ID NO:31), wherein upper case indicates the probe element or tail, lower case defines the template-specific primer region, lower case italics indicates bases that are mismatched to the target, and the bold face base indicates the variable position on the template after the Snapback hairpin has formed. The PCR product was 120 bp in length.

Using a Snapback primer with an "A" at the variable position, all possible matched, partially matched, and completely mismatched templates were investigated. With homozygous templates, one matched and three mismatched duplexes were formed (FIG. 11A), all showing single melting transitions. At the amplicon transition, the G and C PCR products are slightly more stable than the A and T PCR products. The probe element transition is most stable with an A:T match, followed by an A:G mismatch, an A:A mismatch and finally a A:C mismatch.

FIG. 11B shows the matched template along with all three partially matched heterozygotes. As in FIG. 11A, the matched template shows a single probe element melting peak around 68°. All three heterozygotes show composite probe element melting peaks with one allele matched and the other mismatched, usually resolving into two distinct peaks with one peak around 68° C. and the other peak depending upon the particular mismatch.

FIG. 11C shows the matched template along with three heterozygotes with both alleles mismatched. The matched duplex is most stable, while the mismatched heterozygotes form less stable duplexes with the probe element. Each heterozygote melts in a unique broad apparent single transition composed of two mismatched components that are not resolved into distinct peaks.

EXAMPLE 8

Effect of Mismatch Position within the Probe Element of Snapback Primers

Snapback primers with different probe elements were used to amplify the same target sequence. The probe elements were designed to place the variable base at different positions along the probe element, with the same length amplicon. The probe element length was 22 bases, with the variable base placed at position 2, 8, 14, or 20, resulting in loop lengths of 26 to 44 bases and an amplicon size of 120 bps. Although the loop lengths varied up to a maximum of an 18 base difference, this should only affect the absolute Tm and not the ability to distinguish homozygotes from heterozygotes. Asymmetric PCR was performed as in Example 3. The M13 primers used are shown in Table 5, wherein upper case indicates the probe element or tail, lower case defines the template-specific primer region, lower case italics indicates bases that are mismatched to the target, and the bold face base indicates the variable position on the template after the Snapback hairpin has formed.

exon 11. Genotyped human genomic DNA samples were obtained from Coriell Institute for Medical Research (Camden, N.J.) and used at 50 ng/µl in the PCR. The limiting forward primer was tgtgcctttcaaattcagattg (SEQ ID NO:36) (0.05 µM) and the reverse snapback primer was ctGAAAGACAATATAGTTCTTGGAGAcagcaaatgcttgctagacc (SEQ ID NO:37) (0.5 µM). The sequence of the probe element matched the wild type target sequence. The amplicon size was 228 bps. PCR was performed as in Example 3, except that an initial denaturation at 95° C. for 20 s was performed, the annealing temperature was 53° C., 55 cycles were performed, and the melting analysis was done at 0.2° C./s from 55 to 88° C. The Snapback primer loop size was 88 bases and the probe element was 24 bases.

The resultant Snapback primer genotyping is shown in FIG. 13. Derivative melting curves are shown with the higher temperature amplicon melting peak on the right, and the lower temperature probe element peaks are on the left. Melting of the probe element from the mismatched template occurs at about 63° C., while the matched template melts at about 68° C. All three genotypes are easy to discern.

TABLE 5

| Name | |
|---|---|
| | Limiting Forward Primer (0.05 µM) |
| 1F | tcattctcgttttctgaactg (SEQ ID NO: 5) |
| | Snapback Reverse Primer (0.5 µM) |
| 1R22Tmis2 | *ac*AATATTTATGACGATTCCGCAGatgtttagactggatagcgt (SEQ ID NO: 32) |
| 1R22Tmis8 | *gc*TCAATGAATATTTATGACGATTatgtttagactggatagcgt (SEQ ID NO: 33) |
| 1R22Tmis14 | *ct*GGGGATTCAATGAATATTTATatgtttagactggatagcgt (SEQ ID NO: 34) |
| 1R22Tmis20 | *ag*TTTGAGGGGGATTCAATGAATAatgtttagactggatagcgt (SEQ ID NO: 35) |

Both the homozygous "A" template, and a heterozygous "A/G" template were separately amplified in order to test the ability to detect heterozygotes under different positions of the probe element. When the variable base was placed near either end of the probe at position 2 or 20 of a 22 base probe element, it was difficult to distinguish heterozygotes from homozygotes (FIGS. 12A-B). In contrast, when the variable base was near the center at positions 8 or 14, heterozygotes were easily identified (FIGS. 12C-D). These results suggest that in conditions similar to those of this Example, the probe should be near the center of the region of sequence variation if optimal discrimination is desired. Sequence variations close to either of the probe element ends may not be detected.

EXAMPLE 9

Genotyping of the Cystic Fibrosis G542x Mutation with Snapback Primers

Snapback primer genotyping was performed for the CFTR mutation G542X, a single base change of G to T in

EXAMPLE 10

Genotyping of Cystic Fibrosis Exon 10 Sequence Variants (F508del, F507del, and F508C) with Snapback Primers Snapback primer genotyping was performed at the CFTR mutation hotspot in exon 10, including, F507del, F508del, and F508C. Genotyped human genomic DNA samples were obtained from Coriell Institute for Medical Research (Camden, N.J.) and used at 50 ng/µl in the PCR. The limiting forward primer was acttctaatgatgattatggg (SEQ ID NO:38) (0.05 µM) and the reverse Snapback primer was tcAATAT-CATCTTTGGTGTTTCCTATGATGacatagtttcttacctcttc (SEQ ID NO:39) (0.5 µM). The sequence of the probe element matched the wild type sequence. The amplicon size was 231 bps and the Snapback primer loop size was 58 bases.

The resultant Snapback primer probe element melting curves are shown in FIGS. 14A-B, as both derivative (FIG. 14A) and normalized melting curve (FIG. 14B) plots. Melting of the probe element from the wild type template occurs at about 72° C., while the mismatched templates melt at

19 lower temperatures, with each genotype having a characteristic melting curve. All genotypes are easy to distinguish.

EXAMPLE 11

Multi-Locus Genotyping with Bilateral Snapback Primers

Snapback genotyping can be multiplexed along the temperature axis, similar to other melting techniques (9). For example, two or more sets of primers (each with one Snapback primer) can be used to amplify and genotype multiple loci, illustratively by having all alleles separated in melting temperature with their respective probe elements. Alternatively, multiple loci within an amplicon can be genotyped with amplification using two Snapback primers, or one Snapback primer and one unlabeled probe, each of which may interrogate more than one loci by looping out the template between constant regions (13).

When two Snapback primers are used to amplify a single target nucleic acid, illustratively, symmetric PCR may be used to result in sufficient concentration of both product strands. In the present example, the CFTR gene was amplified using symmetric PCR, with each primer at 0.5 µM. The primers included a two-base 5'-end mismatch and either a 17-base (Snapback 1) or a 28-base (Snapback 2) probe element producing a 249 bp PCR product of exon 10 of CFTR with hairpin loops of 69 and 66 bases, respectively. Template DNA concentrations were 5 ng/µl. Reaction volumes of 2 µl in a 96-well plate were overlaid with 10-15 µL of mineral oil (Sigma), the plate was centrifuged (1500 g for 3-5 min), and PCR performed in a PTC-200 thermal cycler (Bio-Rad). An initial denaturation was performed at 95° C. for 3 minutes, followed by 35 cycles of 95° C. for 15 seconds, 55° C. for 10 seconds, and 72° C. for 15 seconds.

Since formation of double-stranded full-length amplicon is an intermolecular reaction that is dependent on concentration, and the Snapback hairpin loop formation is an intramolecular reaction that is generally independent of concentration, dilution of the PCR product will favor Snapback loop formation, as compared to the same undiluted PCR product. Thus, in this illustrative example, after PCR, the CFTR samples were diluted with water (18 µl for a 10× dilution), centrifuged, heated to 95° C. (above the melting temperature for the full-length amplicon) in a LightScanner®, removed from the instrument for cooling to <40° C. (room temperature, which is below the melting temperature for the hairpins of this example), followed by fluorescence acquisition during heating at 0.15° C./s on a LightScanner. It has been found that heating and cooling, illustratively rapid cooling (illustratively at least 2° C./s, and more illustratively at least 5° C./s), subsequent to dilution and prior to fluorescence acquisition melting produced good signal from Snapback hairpins. Only weak hairpin melting transitions were observed in symmetric PCR (i) without dilution or (ii) with dilution and without the heating and cooling prior to fluorescence acquisition during melting. It is understood that other methods may be used to favor the Snapback intramolecular loop formation, such as adjusting pH.

Snapback 1 covered the F508del, 1507del, F508C, and 1506V variants with melting transitions between 46-60° C. The longer Snapback 2 covered the Q493x variant and melted between 66-72° C. Data are displayed in FIG. 15 as a negative derivative plot after normalization and background subtraction. Wild type (circles), compound F508del/Q493x heterozygote (connected small diamonds), 1506V heterozygote (small diamonds), F508C heterozygote (small squares), 1507del heterozygote (large squares), F508del heterozygote (connected large diamonds), and F508del homozygote (connected squares) were all distinguishable.

While a ten-fold dilution was used in this example, it is understood that other dilution ratios may be used, depending on the extent of minimization of signal from the full-length amplicon desired. If only genotyping is desired, a higher dilution may be appropriate, whereas if genotyping and scanning are both desired, a lower dilution may be appropriate. Alternatively, the sample can be melted for scanning without dilution, then melted again after dilution for genotyping. Further, while the PCR amplification product was diluted in this example, it may be possible to obtain a similar result by stopping the PCR amplification prior to the plateau phase, thereby limiting the quantity of full-length amplicon, with resultant lower concentration of the amplicon.

Additional methods of favoring Snapback loop formation over full length amplicon duplexes after symmetric PCR have been demonstrated. For example, this hairpin formation can be favored by rapid cooling after denaturation. This can be achieved in capillaries on the LightCycler by cooling at a programmed rate of −20° C./s and has also been observed at −10° C./s and −5° C./s. Alternatively, rapid cooling sufficient to favor hairpins can be obtained by cooling on block thermocyclers such as the MJ PTC-200, wherein denatured samples were cooled to <35° C. in 60 seconds. Hairpin formation after denaturation can be highly favored by cooling denatured samples in capillaries by plunging them in ice water, where temperature <5° C. can be obtained in less than 2 seconds. If samples are rapidly cooled, they do not necessarily need to be diluted after symmetric PCR, depending on the amounts of hairpin and full length amplicon duplex desired.

High pH, illustratively from pH 8.5 to 11.0, also favors formation of hairpins over full length duplex amplicons. PCR can either be performed at high pH, or the pH increased after PCR, illustratively by adding a dilute solution of NaOH or a high pH buffer. For example, hairpin formation is favored after PCR amplification in AMP (aminomethyl propanol) buffers from pH 8.9 to 10.8. Alternatively, PCR can be performed in 10 mM Tris buffer, pH 8.5, and 10 mM AMP buffers between pH 9 and 11 added after PCR to make the solution more basic. Dilute unbuffered NaOH can also be added directly, for example, 1-9 µl of 0.01 M NaOH may be added into the reaction products of a 10 µl PCR buffered with 10 mM Tris, pH 8.5. In summary, the amplification product may be adjusted by a combination of one or more of the following to favor hairpin formation over intermolecular hybridization: 1) lower product concentration, illustratively obtained either by limiting the amount of PCR product produced (low number of cycles or low primer concentrations), or by diluting after PCR; 2) rapid cooling after denaturation; and 3) high pH (illustratively 8.5-11.0) obtained either by running the PCR at high pH or by adding a basic solution after PCR is completed.

EXAMPLE 12

Snapback Primers as an Energy Transfer Donor for Multicolor Genotyping

Even greater multiplexing would be possible if different probe elements could be "colored" with different fluorophores. This approach has been shown with iFRET (induced fluorescence resonance energy transfer), where a solution of a dsDNA dye (SYBR Green I) in the presence of a DNA duplex provides donor fluorescence to an acceptor dye covalently attached to a strand of the duplex (14).

To demonstrate resonance energy transfer and the feasibility of color multiplexing with Snapback primers, a Snapback primer with a 5'-terminal, covalently-attached dye, LCRed640 (Roche Diagnostics) was compared to a 5'-labeled probe of the same sequence. For the Snapback amplification, the forward primer sequence was 1F (tcattctcgttttct-gaactg (SEQ ID NO:5)) and the Snapback primer was Red640-GGATTCAATGAATATTTATGACGAatgttta-gactggatagcgt (SEQ ID NO:15). For the labeled probe reaction used as a control, the forward primer was again 1F, the reverse primer was 1R (atgtttagactggatagcgt (SEQ ID NO:40)) and the labeled probe was Red640-GGATTCAAT-GAATATTTATGACGA-P (SEQ ID NO:41), where "P" is a 3'-phosphate. PCR was performed in the presence of 0.5× LCGreen Plus as described in Example 3 except that the extension temperature was 74° C., 50 cycles were performed, the forward primer concentration was 0.1 µM, the reverse primer concentration (Snapback or normal) was 0.5 µM, and the labeled probe (if present) was at 0.5 µM. Melting analysis was performed on the LightCycler® in the F2 (LCRed640) channel at 0.2 C/s from 50-87° C.

FIG. 16 shows derivative melting plots in the LCRed640 channel that demonstrate resonance energy transfer between LCGreen Plus and covalently attached LCRed640. LCRed640 melting transitions are apparent using either Snapback primers or labeled probes, although the intramolecular loop stabilizes the Snapback duplex by about 9° C. relative to the intermolecular duplex. By labeling different Snapback primer with different fluorophores that are excited by the same dsDNA dye (e.g. LCGreen Plus), color multiplexing can be achieved. Color compensation techniques, preferably methods that account for the effect of temperature on crosstalk between channels (9), are used to de-convolute the complex spectral signal into individual components.

In FIG. 16 the labeled probe control reaction reveals a melting peak at 63° C., a result of FRET between bound LCGreen Plus and the labeled probe. The labeled Snapback primer, stabilized by about 9° C. from intramolecular binding, has a melting temperature of about 72° C.

EXAMPLE 13

Combined Snapback Genotyping and Amplicon Scanning

Asymmetric amplification with Snapback primers produces both a hairpin for genotyping and double stranded product for amplicon scanning. Hence, both genotyping and scanning from the same melting curve is possible with Snapback primers. A schematic for such a method is shown in FIG. 17. Because Snapback genotyping is usually done with asymmetric PCR, the amplicon signal is not as strong as with symmetric amplification, and the heterozygote scanning accuracy is currently unknown. Nevertheless, the potential to screen for mutations and genotype specific sequence variants in one process is attractive and can potentially eliminate 99% of the sequencing burden in whole gene analysis. Any sequence difference in the sequence between the primers skews the amplicon melting transition to lower temperatures because of the heteroduplexes formed. In addition, with Snapback hairpins, common variants under the probe element can be definitively identified. Homozygous variants are also identified by the probe element, but may not alter amplicon melting. Finally, if the amplicon transition indicates a heterozygous variant but the Snapback transition is normal, a rare or new variant outside of the probed region is suggested and may require sequencing for identification.

As an alternative to asymmetric PCR, scanning and genotyping may be done in two steps using a Snapback primer and symmetric PCR, with and without dilution. As discussed above, symmetric PCR to plateau phase favors formation of full-length double-stranded amplicon, while dilution favors Snapback loop formation. The primers were tctcagggtattttatgagaaataaatgaa (SEQ ID NO:42) and gtAAGGAGGAACGCTCTATCtcctcacaataataaagagaaggca (SEQ ID NO:43) and amplified a 211 bp PCR product including exon 4 of CFTR. The hairpin loop was 46 bases with a hairpin duplex length of 18 bps. PCR was performed as in Example 11 except that 5 µl volumes were used with 2 mM $Mg^{++}$ and 0.25 µM of each primer. Temperature cycling included an initial denaturation of 95° C. for 5 mM, followed by 36 cycles of 95° C. for 30 s, 62° C. for 10 s, and 72° C. for 30 s. Melting acquisition for scanning was from 60 to 95° C. before any additions or dilutions. FIG. 18A shows the scanning melting curves of several wild type samples and a single R117H heterozygote resulting from a G to A base change. The single R117H heterozygote is clearly visible, indicating that such symmetric melting curves without dilution may be used for scanning FIG. 18B shows a derivative plot of the same amplification product subsequent to dilution with 45 µl water (10× dilution) and heating and cooling as discussed above prior to melting data acquisition. Again, the R117H heterozygote is easily distinguishable for specific identification by snapback primer genotyping. While the same heterozygote is seen in both curves, this demonstrates that it is possible to scan and genotype with the same PCR amplification using a Snapback primer.

EXAMPLE 14

Haplotyping with Snapback Primers

By combining allele-specific amplification with Snapback primer genotyping, a simple method for haplotyping is provided. Consider two genetic loci, A and B, each with two alleles, A1, A2, and B1, B2. The primer element of a Snapback primer is designed to anneal to the A locus, and the probe element of the Snapback primer is designed to anneal to the B locus, with the second primer designed to flank the B locus, so that the B locus is amplified by the two primers. If the Snapback primer is designed only to extend allele 1 of the A locus (illustratively by placing the 3' end at the variable position of the A locus), then the B locus type identified by melting the probe element must be associated with (the same haplotype as) the A1 allele. Thus, if the primer element extends A1, the probe element matches B1, and the probe melting curve indicates a match, a A1B1 haplotype is present. If the probe melting curve indicates a mismatch, an A1B2 haplotype is present. If the primer element extends A2, the probe element matches B1, and the probe melting curve indicates a match, an A2B1 haplotype is present. If the probe melting curve indicates a mismatch, an A2B2 haplotype is present.

REFERENCES (herein incorporated in their entireties)

1. Lee L G, Connell C R, Bloch W. Allelic discrimination by nick-translation PCR with fluorogenic probes. Nucleic Acids Res. 1993 Aug. 11; 21(16):3761-6.

2. Whitcombe D, Theaker J, Guy S P, Brown T, Little S. Detection of PCR products using self-probing amplicons and fluorescence. Nat Biotechnol 1999; 17:804-7.

3. Solinas A, Brown L J, McKeen C, Mellor J M, Nicol J, Thelwell N, Brown T. Duplex Scorpion primers in SNP analysis and FRET applications. Nucleic Acids Res 2001; 29:E96.

4. Thelwell N, Millington S, Solinas A, Booth J, Brown T. Mode of action and application of Scorpion primers to mutation detection. Nucleic Acids Res 2000; 28:3752-61.

5. Wilton S D, Honeyman K, Fletcher S, Laing N G. Snapback SSCP analysis: engineered conformation changes for the rapid typing of known mutations. Hum Mutat 1998; 11:252-8.

6. Shendure J, Porreca G J, Reppas N B, Lin X, McCutcheon J P, Rosenbaum A M, Wang M D, Zhang K, Mitra R D, Church G M. Accurate multiplex polony sequencing of an evolved bacterial genome. Science 2005; 309:1728-32.

7. Wetmur J G, Kumar M, Zhang L, Palomeque C, Wallenstein S, Chen J. Molecular haplotyping by linking emulsion PCR: analysis of paraoxonase 1 haplotypes and phenotypes. Nucleic Acids Res 2005; 33:2615-9.

8. Reed G H, Wittwer C T. Sensitivity and specificity of single-nucleotide polymorphism scanning by high-resolution melting analysis. Clin Chem 2004; 50:1748-54.

9. Wittwer C T, Herrmann M G, Gundry C N, Elenitoba-Johnson K S. Real-time multiplex PCR assays. Methods 2001; 25:430-42.

10. Wittwer C T, Herrmann M G, Moss A A, Rasmussen R P. Continuous fluorescence monitoring of rapid cycle DNA amplification. Biotechniques 1997; 22:130-1, 4-8.

11. Zhou L, Myers A N, Vandersteen J G, Wang L, Wittwer C T. Closed-tube genotyping with unlabeled oligonucleotide probes and a saturating DNA dye. Clin Chem 2004; 50:1328-35.

12. Wittwer C T, Reed G H, Gundry C N, Vandersteen J G, Pryor R I. High-resolution genotyping by amplicon melting analysis using LCGreen. Clin Chem 2003; 49:853-60.

13. Pont-Kingdon G, Lyon E. Direct molecular haplotyping by melting curve analysis of hybridization probes: beta 2-adrenergic receptor haplotypes as an example. Nucleic Acids Res 2005; 33:e89.

14. Howell W M, Jobs M, Brookes A L iFRET: an improved fluorescence system for DNA-melting analysis. Genome Res 2002; 12:1401-7.

15. Wittwer C T, et al., Real-Time PCR. In: Persing D, et al., eds. Diagnostic Molecular Microbiology: Principles and Applications. ASM Press, 2004.

16. Aoshima T, Sekido Y, Miyazaki T, Kajita M, Mimura S, Watanabe k, Shimokata K, Niwa T. Rapid Detection of Deletion Mutations in Inherited Metabolic Diseases by Melting Curve Analysis with LightCycler. Clin Chem 2000; 46:119-22.

17. Marziliano N, Pelo E, Minuti B, Passerini I, Torricelli F, Da Prato L. Melting Temperature Assay for a UGT1A Gene Variant in Gilbert Syndrome. Clin Chem 2000; 46:423-55.

18. Lipsky R H, Mazzanti C, Rudolph J, Xu K, Vyas G, Bozak D, Radel M, Goldman D. DNA Melting Analysis for Detection of Single Nucleotide Polymorphisms. Clin Chem 2001; 47:635-44.

19. Pirulli D, Boniotto M, Puzzer D, Spanò A, Amoroso A, Crovella S. Flexibility of Melting Temperature Assay for Rapid Detection of Insertions, Deletions, and Single-Point Mutations of the AGXT Gene Responsible for Type 1 Primary Hyperoxaluria. Clin Chem 2000; 46:1842-44.

20. Tanriverdi S, Tanyeli A, Baslamisli F, Köksal F, Kilinç Y, Feng X, Batzer G, Tzipori S, Widmer G. Detection and Genotyping of Oocysts of *Cryptosporidium parvum* by Real-Time PCR and Melting Curve Analysis. J Clin Microbiol. 2002; 40:3237-44.

21. Hladnik U, Braida L, Boniotto M, Pirulli D, Gerin F, Amoroso A, Crovella S. Single-tube genotyping of MBL-2 polymorphisms using melting temperature analysis. Clin Exp Med. 2002; 2:105-08.

22. von Ahsen N, Oellerich M, Schütz E. Limitations of Genotyping Based on Amplicon Melting Temperature. Clin Chem 2001; 47:1331-1332.

23. Douthart R J, Burnett J, Beasley F, Frank B, Binding of Ethidium Bromide to Double-Stranded Ribonucleic Acid. Biochemistry 1973; 12:214-20.

24. Aktipis S, Martz W, Kindelis A. Thermal Denaturation of the DNA-Ethidium Complex. Redistribution of the Intercalated Dye During Melting. Biochemistry 1975; 14:326-31.

25. Highsmith W E, Jr., Jin Q, Nataraj A J, O'Connor J M, Burland V D, Baubonis W R, Curtis F P, Kusukawa N, Garner M M. Use of a DNA toolbox for the characterization of mutation scanning methods. I: construction of the toolbox and evaluation of heteroduplex analysis. Electrophoresis 1999; 20:1186-94.

26. Margraf R L, Mao R, Wittwer C T. Masking selected sequence variation by incorporating mismatches into melting analysis probes. Hum Mutat. 2006 Mar.; 27(3):269-78.

Although the invention has been described in detail with reference to preferred embodiments, variations and modifications exist within the scope and spirit of the invention as described and defined in the following claims.

The invention claimed is:

1. A method for nucleic acid analysis comprising the steps of
mixing a target nucleic acid with a first primer, a second primer, and a dsDNA binding dye to form a mixture, the primers configured for amplifying the target nucleic acid, wherein the first primer comprises a probe element specific for a locus of the target nucleic acid and a template-specific primer region, wherein the probe element is 5' of the template-specific primer region, and wherein the dsDNA binding dye is not covalently bound to the first primer,
amplifying the target nucleic acid in the mixture by means of the primers to generate an amplicon, the amplicon comprising the probe element and the locus,
allowing the probe element of the amplicon to hybridize intramolecularly to the locus of the amplicon to form a hairpin,
heating the mixture to melt the hairpin, and
generating a melting curve for the probe element by measuring fluorescence from the dsDNA binding dye as the mixture is heated to melt the hairpin, wherein the melting curve for the probe element is distinguishable from a melting curve for double-stranded amplicon.

2. The method of claim 1 wherein the first primer is provided in the mixture at a concentration greater than the second primer for asymmetric amplification.

3. The method of claim 1 wherein the amplifying step is amplifying by PCR.

4. The method of claim 1 wherein the first primer further comprises a mismatched region 5' of the probe element.

5. The method of claim 1 wherein the first primer is an oligonucleotide that does not have any covalently attached dyes or quenchers.

6. The method of claim 5 wherein the first primer does not have an extension blocker.

7. The method of claim 1 wherein the dsDNA binding dye is a saturation dye.

8. The method of claim 7 wherein the dye is present at concentrations sufficient to distinguish heterozygotes in the melting curve for the probe element.

9. The method of claim 1 wherein the first and second primers are provided in the mixture at essentially the same concentration, and wherein the second primer comprises a probe element specific for a second locus of the target nucleic acid and a 30 template-specific primer region, wherein the probe element of the second primer is 5' of the template-specific primer region.

10. The method of claim 9 further comprising the step of diluting the amplicon prior to generating the melting curve for the probe element.

11. The method of claim 10 further comprising the step of heating the diluted amplicon to at least a denaturation temperature of the amplicon and cooling the heated diluted amplicon to a temperature below a denaturation temperature of the hairpin prior to generating the melting curve for the probe element.

12. The method of claim 11 wherein the cooling is rapid cooling.

13. The method of claim 9 wherein the first primer comprises an extension blocker between the probe element and the template-specific primer region.

14. The method of claim 1 wherein the hairpin has a loop of between 20 and 50 bases.

15. The method of claim 1 wherein the probe element is less than 20 bases.

16. The method of claim 15 wherein the probe element is less than 10 bases.

17. The method of claim 16 wherein the probe element is 6 bases.

18. The method of claim 1 wherein the mixture further comprises a third primer, the third primer comprises a probe element specific for a third locus of the target nucleic acid and a template-specific primer region, wherein the third primer's template-specific primer region is the same as the first primer's template-specific primer region, but the third primer's probe element is specific for a locus that is distinct from the locus of the first primer's probe element.

19. The method of claim 1 wherein the locus has a known single nucleotide polymorphism, and the single nucleotide polymorphism is located no closer than 8 bases from an end of the probe element.

20. The method of claim 1 wherein the mixture further comprises an unlabeled probe configured to hybridize to a different locus of the target nucleic acid.

21. The method of claim 1 wherein
the second primer comprises a probe element specific for a second locus of the target nucleic acid, a template-specific primer region and a covalently bound dye capable of resonance energy transfer with the dsDNA binding dye, wherein the probe element of the second primer is 5' of the template-specific primer region, and the fluorescence of the dsDNA binding dye is measured at a first wavelength and the generating step further includes measuring fluorescence from the covalently bound dye at a second wavelength.

22. The method of claim 1 wherein the target nucleic acid further comprises a second locus, and the template-specific primer region of the first primer is configured to amplify the target nucleic acid only if a particular allele of the second locus is present.

23. The method of claim 1 further comprising the step of analyzing the shape of the melting curve for the probe element.

24. The method of claim 1 wherein the mixture is adjusted to favor probe element binding intramolecularly prior to generating the melting curve for the probe element.

25. The method of claim 1 wherein amplification is terminated prior to reaching plateau phase, to limit amplicon concentration.

26. A method for nucleic acid analysis comprising the steps of mixing a target nucleic acid with a first primer, a second primer, and a dsDNA binding dye to form a mixture, the primers configured for amplifying the target nucleic acid, wherein the first primer comprises a probe element specific for a locus of the target nucleic acid and a template-specific primer region, wherein the probe element is 5' of the template-specific primer region, and wherein the dsDNA binding dye is not covalently bound to the first primer, amplifying the target nucleic acid in the mixture to generate an amplicon, the amplicon comprising the probe element and the locus, adjusting the mixture to favor hairpin formation by the probe element binding intramolecularly to the target nucleic acid, and generating a melting curve for the probe element by measuring fluorescence from the dsDNA binding dye as the mixture is heated to melt the hairpin, wherein the melting curve for the probe element is distinguishable from a melting curve for the amplicon.

27. The method of claim 1, wherein the amplicon is double-stranded, the melting curve for the probe element being distinguishable from the melting curve for the double-stranded amplicon.

28. The method of claim 26, wherein the amplicon is double-stranded, the melting curve for the probe element being distinguishable from the melting curve for the double-stranded amplicon.

* * * * *

SEQUENCE LISTING

```
<160> NUMBER OF SEQ ID NOS: 43

<210> SEQ ID NO 1
<211> LENGTH: 49
<212> TYPE: DNA
<213> ORGANISM: Artificial Sequence
<220> FEATURE:
<223> OTHER INFORMATION: synthetic plasmid
<220> FEATURE:
<221> NAME/KEY: misc_binding
<222> LOCATION: (1)..(28)
<223> OTHER INFORMATION: probe binding position for Snapback primer
<220> FEATURE:
<221> NAME/KEY: primer_bind
<222> LOCATION: (29)..(49)
```

<400> SEQUENCE: 1
aatcgtcata aatattcatt gaatcccctc attctcgttt tctgaactg       49

<210> SEQ ID NO 2
<211> LENGTH: 20
<212> TYPE: DNA
<213> ORGANISM: Artificial Sequence
<220> FEATURE:
<223> OTHER INFORMATION: synthetic plasmid
<220> FEATURE:
<221> NAME/KEY: primer_bind
<222> LOCATION: (1)..(20)

<400> SEQUENCE: 2
atgtttagac tggatagcgt                                       20

<210> SEQ ID NO 3
<211> LENGTH: 59
<212> TYPE: DNA
<213> ORGANISM: Artificial Sequence
<220> FEATURE:
<223> OTHER INFORMATION: synthetic plasmid
<220> FEATURE:
<221> NAME/KEY: misc_binding
<222> LOCATION: (1)..(28)
<223> OTHER INFORMATION: probe binding region for Snapback primer
<220> FEATURE:
<221> NAME/KEY: misc_feature
<222> LOCATION: (29)..(38)
<223> OTHER INFORMATION: ten base tetrahydrofuran derivative extension
      blocker
<220> FEATURE:
<221> NAME/KEY: primer_bind
<222> LOCATION: (39)..(55)

<400> SEQUENCE: 3
aatcgtcata aatattcatt gaatccccnn nnnnnnnntc attctcgttt tctgaactg    59

<210> SEQ ID NO 4
<211> LENGTH: 20
<212> TYPE: DNA
<213> ORGANISM: Artificial Sequence
<220> FEATURE:
<223> OTHER INFORMATION: primer for artificial plasmid
<220> FEATURE:
<221> NAME/KEY: primer_bind
<222> LOCATION: (1)..(20)

<400> SEQUENCE: 4
atgtttagac tggatagcgt                                       20

<210> SEQ ID NO 5
<211> LENGTH: 21
<212> TYPE: DNA
<213> ORGANISM: Artificial Sequence
<220> FEATURE:
<223> OTHER INFORMATION: primer for artificial plasmid
<220> FEATURE:
<221> NAME/KEY: primer_bind
<222> LOCATION: (1)..(20)

<400> SEQUENCE: 5
tcattctcgt tttctgaact g                                     21

<210> SEQ ID NO 6
<211> LENGTH: 26
<212> TYPE: DNA
<213> ORGANISM: Artificial Sequence
<220> FEATURE:

```
<223> OTHER INFORMATION: primer for artificial plasmid
<220> FEATURE:
<221> NAME/KEY: misc_binding
<222> LOCATION: (1)..(6)
<223> OTHER INFORMATION: probe binding region for Snapback primer
<220> FEATURE:
<221> NAME/KEY: primer_bind
<222> LOCATION: (7)..(26)

<400> SEQUENCE: 6
gaatatatgt ttagactgga tagcgt                                              26

<210> SEQ ID NO 7
<211> LENGTH: 28
<212> TYPE: DNA
<213> ORGANISM: Artificial Sequence
<220> FEATURE:
<223> OTHER INFORMATION: primer for artificial plasmid
<220> FEATURE:
<221> NAME/KEY: misc_binding
<222> LOCATION: (1)..(8)
<223> OTHER INFORMATION: probe binding region for Snapback primer
<220> FEATURE:
<221> NAME/KEY: primer_bind
<222> LOCATION: (9)..(28)

<400> SEQUENCE: 7
tgaatattat gtttagactg gatagcgt                                            28

<210> SEQ ID NO 8
<211> LENGTH: 30
<212> TYPE: DNA
<213> ORGANISM: Artificial Sequence
<220> FEATURE:
<223> OTHER INFORMATION: primer for artificial plasmid
<220> FEATURE:
<221> NAME/KEY: misc_binding
<222> LOCATION: (1)..(10)
<223> OTHER INFORMATION: probe binding region for Snapback primer
<220> FEATURE:
<221> NAME/KEY: primer_bind
<222> LOCATION: (11)..(30)

<400> SEQUENCE: 8
atgaatattt atgtttagac tggatagcgt                                          30

<210> SEQ ID NO 9
<211> LENGTH: 32
<212> TYPE: DNA
<213> ORGANISM: Artificial Sequence
<220> FEATURE:
<223> OTHER INFORMATION: primer for artificial plasmid
<220> FEATURE:
<221> NAME/KEY: misc_binding
<222> LOCATION: (1)..(12)
<223> OTHER INFORMATION: probe binding region for Snapback primer
<220> FEATURE:
<221> NAME/KEY: primer_bind
<222> LOCATION: (13)..(32)

<400> SEQUENCE: 9
aatgaatatt taatgtttag actggatagc gt                                       32

<210> SEQ ID NO 10
<211> LENGTH: 34
<212> TYPE: DNA
<213> ORGANISM: Artificial Sequence
<220> FEATURE:
<223> OTHER INFORMATION: primer for artificial plasmid
<220> FEATURE:
<221> NAME/KEY: misc_binding
```

```
<222> LOCATION: (1)..(14)
<223> OTHER INFORMATION: probe binding region for Snapback primer
<220> FEATURE:
<221> NAME/KEY: primer_bind
<222> LOCATION: (15)..(34)

<400> SEQUENCE: 10
caatgaatat ttatatgttt agactggata gcgt                                   34

<210> SEQ ID NO 11
<211> LENGTH: 36
<212> TYPE: DNA
<213> ORGANISM: Artificial Sequence
<220> FEATURE:
<223> OTHER INFORMATION: primer for artificial plasmid
<220> FEATURE:
<221> NAME/KEY: misc_binding
<222> LOCATION: (1)..(16)
<223> OTHER INFORMATION: probe binding region for Snapback primer
<220> FEATURE:
<221> NAME/KEY: primer_bind
<222> LOCATION: (17)..(36)

<400> SEQUENCE: 11
tcaatgaata tttatgatgt ttagactgga tagcgt                                 36

<210> SEQ ID NO 12
<211> LENGTH: 38
<212> TYPE: DNA
<213> ORGANISM: Artificial Sequence
<220> FEATURE:
<223> OTHER INFORMATION: primer for artificial plasmid
<220> FEATURE:
<221> NAME/KEY: misc_binding
<222> LOCATION: (1)..(18)
<223> OTHER INFORMATION: probe binding region for Snapback primer
<220> FEATURE:
<221> NAME/KEY: primer_bind
<222> LOCATION: (19)..(38)

<400> SEQUENCE: 12
ttcaatgaat atttatgaat gtttagactg gatagcgt                               38

<210> SEQ ID NO 13
<211> LENGTH: 40
<212> TYPE: DNA
<213> ORGANISM: Artificial Sequence
<220> FEATURE:
<223> OTHER INFORMATION: primer for artificial plasmid
<220> FEATURE:
<221> NAME/KEY: misc_binding
<222> LOCATION: (1)..(20)
<223> OTHER INFORMATION: probe binding region for Snapback primer
<220> FEATURE:
<221> NAME/KEY: primer_bind
<222> LOCATION: (20)..(40)

<400> SEQUENCE: 13
attcaatgaa tatttatgac atgtttagac tggatagcgt                             40

<210> SEQ ID NO 14
<211> LENGTH: 42
<212> TYPE: DNA
<213> ORGANISM: Artificial Sequence
<220> FEATURE:
<223> OTHER INFORMATION: primer for artificial plasmid
<220> FEATURE:
<221> NAME/KEY: misc_binding
<222> LOCATION: (1)..(22)
<223> OTHER INFORMATION: probe binding region for Snapback primer
<220> FEATURE:
```

```
<221> NAME/KEY: primer_bind
<222> LOCATION: (23)..(42)

<400> SEQUENCE: 14
gattcaatga atatttatga cgatgtttag actggatagc gt                          42

<210> SEQ ID NO 15
<211> LENGTH: 44
<212> TYPE: DNA
<213> ORGANISM: Artificial Sequence
<220> FEATURE:
<223> OTHER INFORMATION: primer for artificial plasmid
<220> FEATURE:
<221> NAME/KEY: misc_binding
<222> LOCATION: (1)..(24)
<223> OTHER INFORMATION: probe binding region for Snapback primer
<220> FEATURE:
<221> NAME/KEY: primer_bind
<222> LOCATION: (25)..(44)

<400> SEQUENCE: 15
ggattcaatg aatatttatg acgaatgttt agactggata gcgt                        44

<210> SEQ ID NO 16
<211> LENGTH: 46
<212> TYPE: DNA
<213> ORGANISM: Artificial Sequence
<220> FEATURE:
<223> OTHER INFORMATION: primer for artificial plasmid
<220> FEATURE:
<221> NAME/KEY: misc_binding
<222> LOCATION: (1)..(26)
<223> OTHER INFORMATION: probe binding region for Snapback primer
<220> FEATURE:
<221> NAME/KEY: primer_bind
<222> LOCATION: (27)..(46)

<400> SEQUENCE: 16
gggattcaat gaatatttat gacgatatgt ttagactgga tagcgt                      46

<210> SEQ ID NO 17
<211> LENGTH: 30
<212> TYPE: DNA
<213> ORGANISM: Artificial Sequence
<220> FEATURE:
<223> OTHER INFORMATION: primer for artificial plasmid
<220> FEATURE:
<221> NAME/KEY: misc_feature
<222> LOCATION: (1)..(2)
<223> OTHER INFORMATION: two base mismatch
<220> FEATURE:
<221> NAME/KEY: misc_binding
<222> LOCATION: (3)..(10)
<223> OTHER INFORMATION: probe binding region for Snapback primer
<220> FEATURE:
<221> NAME/KEY: primer_bind
<222> LOCATION: (11)..(30)

<400> SEQUENCE: 17
cctgaatatt atgtttagac tggatagcgt                                        30

<210> SEQ ID NO 18
<211> LENGTH: 34
<212> TYPE: DNA
<213> ORGANISM: Artificial Sequence
<220> FEATURE:
<223> OTHER INFORMATION: primer for artificial plasmid
<220> FEATURE:
<221> NAME/KEY: misc_feature
<222> LOCATION: (1)..(2)
<223> OTHER INFORMATION: two base mismatch
```

```
<220> FEATURE:
<221> NAME/KEY: misc_binding
<222> LOCATION: (3)..(14)
<223> OTHER INFORMATION: probe binding region for Snapback primer
<220> FEATURE:
<221> NAME/KEY: primer_bind
<222> LOCATION: (15)..(34)

<400> SEQUENCE: 18
gtaatgaata tttaatgttt agactggata gcgt                                    34

<210> SEQ ID NO 19
<211> LENGTH: 38
<212> TYPE: DNA
<213> ORGANISM: Artificial Sequence
<220> FEATURE:
<223> OTHER INFORMATION: primer for artificial plasmid
<220> FEATURE:
<221> NAME/KEY: misc_feature
<222> LOCATION: (1)..(2)
<223> OTHER INFORMATION: two base mismatch
<220> FEATURE:
<221> NAME/KEY: misc_binding
<222> LOCATION: (3)..(18)
<223> OTHER INFORMATION: probe binding region for Snapback primer
<220> FEATURE:
<221> NAME/KEY: primer_bind
<222> LOCATION: (19)..(38)

<400> SEQUENCE: 19
cgtcaatgaa tatttatgat gtttagactg gatagcgt                                38

<210> SEQ ID NO 20
<211> LENGTH: 42
<212> TYPE: DNA
<213> ORGANISM: Artificial Sequence
<220> FEATURE:
<223> OTHER INFORMATION: primer for artificial plasmid
<220> FEATURE:
<221> NAME/KEY: misc_feature
<222> LOCATION: (1)..(2)
<223> OTHER INFORMATION: two base mismatch
<220> FEATURE:
<221> NAME/KEY: misc_binding
<222> LOCATION: (3)..(22)
<223> OTHER INFORMATION: probe binding region for Snapback primer
<220> FEATURE:
<221> NAME/KEY: primer_bind
<222> LOCATION: (23)..(42)

<400> SEQUENCE: 20
tcattcaatg aatatttatg acatgtttag actggatagc gt                           42

<210> SEQ ID NO 21
<211> LENGTH: 20
<212> TYPE: DNA
<213> ORGANISM: Artificial Sequence
<220> FEATURE:
<223> OTHER INFORMATION: primer for artificial plasmid
<220> FEATURE:
<221> NAME/KEY: primer_bind
<222> LOCATION: (1)..(20)

<400> SEQUENCE: 21
gcaatccgct ttgcttctga                                                    20

<210> SEQ ID NO 22
<211> LENGTH: 20
<212> TYPE: DNA
<213> ORGANISM: Artificial Sequence
<220> FEATURE:
```

```
<223> OTHER INFORMATION: primer for artificial plasmid
<220> FEATURE:
<221> NAME/KEY: primer_bind
<222> LOCATION: (1)..(20)

<400> SEQUENCE: 22
gatatttgaa gtctttcggg                                              20

<210> SEQ ID NO 23
<211> LENGTH: 20
<212> TYPE: DNA
<213> ORGANISM: Artificial Sequence
<220> FEATURE:
<223> OTHER INFORMATION: primer for artificial plasmid
<220> FEATURE:
<221> NAME/KEY: primer_bind
<222> LOCATION: (1)..(20)

<400> SEQUENCE: 23
gttggagttt gcttccggtc                                              20

<210> SEQ ID NO 24
<211> LENGTH: 20
<212> TYPE: DNA
<213> ORGANISM: Artificial Sequence
<220> FEATURE:
<223> OTHER INFORMATION: primer for artificial plasmid
<220> FEATURE:
<221> NAME/KEY: primer_bind
<222> LOCATION: (1)..(20)

<400> SEQUENCE: 24
atgacctctt atcaaaagga                                              20

<210> SEQ ID NO 25
<211> LENGTH: 44
<212> TYPE: DNA
<213> ORGANISM: Artificial Sequence
<220> FEATURE:
<223> OTHER INFORMATION: primer for artificial plasmid
<220> FEATURE:
<221> NAME/KEY: misc_feature
<222> LOCATION: (1)..(1)
<223> OTHER INFORMATION: two base mismatch
<220> FEATURE:
<221> NAME/KEY: misc_binding
<222> LOCATION: (3)..(24)
<223> OTHER INFORMATION: probe binding region for Snapback primer
<220> FEATURE:
<221> NAME/KEY: primer_bind
<222> LOCATION: (25)..(44)

<400> SEQUENCE: 25
tcgattcaat gaatatttat gacgatgttt agactggata gcgt                   44

<210> SEQ ID NO 26
<211> LENGTH: 41
<212> TYPE: DNA
<213> ORGANISM: Artificial Sequence
<220> FEATURE:
<223> OTHER INFORMATION: primer for artificial plasmid
<220> FEATURE:
<221> NAME/KEY: misc_binding
<222> LOCATION: (1)..(24)
<223> OTHER INFORMATION: probe binding region for Snapback primer
<220> FEATURE:
<221> NAME/KEY: primer_bind
<222> LOCATION: (25)..(41)

<400> SEQUENCE: 26
```
ggattcaatg aatatttatg acgacgtcca atactgcgga a                41

```
<210> SEQ ID NO 27
<211> LENGTH: 45
<212> TYPE: DNA
<213> ORGANISM: Artificial Sequence
<220> FEATURE:
<223> OTHER INFORMATION: primer for artificial plasmid
<220> FEATURE:
<221> NAME/KEY: misc_binding
<222> LOCATION: (1)..(24)
<223> OTHER INFORMATION: probe binding region for Snapback primer
<220> FEATURE:
<221> NAME/KEY: primer_bind
<222> LOCATION: (25)..(45)

<400> SEQUENCE: 27
```
ggattcaatg aatatttatg acgaaaaata gcgagaggct tttgc            45

```
<210> SEQ ID NO 28
<211> LENGTH: 44
<212> TYPE: DNA
<213> ORGANISM: Artificial Sequence
<220> FEATURE:
<223> OTHER INFORMATION: primer for artificial plasmid
<220> FEATURE:
<221> NAME/KEY: misc_binding
<222> LOCATION: (1)..(24)
<223> OTHER INFORMATION: probe binding region for Snapback primer
<220> FEATURE:
<221> NAME/KEY: primer_bind
<222> LOCATION: (25)..(44)

<400> SEQUENCE: 28
```
ggattcaatg aatatttatg acgataagag caacactatc ataa             44

```
<210> SEQ ID NO 29
<211> LENGTH: 44
<212> TYPE: DNA
<213> ORGANISM: Artificial Sequence
<220> FEATURE:
<223> OTHER INFORMATION: primer for artificial plasmid
<220> FEATURE:
<221> NAME/KEY: misc_binding
<222> LOCATION: (1)..(24)
<223> OTHER INFORMATION: probe binding region for Snapback primer
<220> FEATURE:
<221> NAME/KEY: primer_bind
<222> LOCATION: (25)..(44)

<400> SEQUENCE: 29
```
ggattcaatg aatatttatg acgaaatgca gatacataac gcca             44

```
<210> SEQ ID NO 30
<211> LENGTH: 44
<212> TYPE: DNA
<213> ORGANISM: Artificial Sequence
<220> FEATURE:
<223> OTHER INFORMATION: primer for artificial plasmid
<220> FEATURE:
<221> NAME/KEY: misc_binding
<222> LOCATION: (1)..(24)
<223> OTHER INFORMATION: probe binding region for Snapback primer
<220> FEATURE:
<221> NAME/KEY: primer_bind
<222> LOCATION: (25)..(44)

<400> SEQUENCE: 30
```
ggattcaatg aatatttatg acgaacaaca ttattacagg taga             44

<210> SEQ ID NO 31
<211> LENGTH: 44
<212> TYPE: DNA
<213> ORGANISM: Artificial Sequence
<220> FEATURE:
<223> OTHER INFORMATION: primer for artificial plasmid
<220> FEATURE:
<221> NAME/KEY: misc_feature
<222> LOCATION: (1)..(2)
<223> OTHER INFORMATION: two base mismatch
<220> FEATURE:
<221> NAME/KEY: misc_binding
<222> LOCATION: (3)..(24)
<223> OTHER INFORMATION: probe binding region for Snapback primer
<220> FEATURE:
<221> NAME/KEY: primer_bind
<222> LOCATION: (25)..(44)

<400> SEQUENCE: 31
tcattcaatg aatatttatg acgaatgttt agactggata gcgt        44

<210> SEQ ID NO 32
<211> LENGTH: 44
<212> TYPE: DNA
<213> ORGANISM: Artificial Sequence
<220> FEATURE:
<223> OTHER INFORMATION: primer for artificial plasmid
<220> FEATURE:
<221> NAME/KEY: misc_feature
<222> LOCATION: (1)..(2)
<223> OTHER INFORMATION: two base mismatch
<220> FEATURE:
<221> NAME/KEY: misc_binding
<222> LOCATION: (3)..(24)
<223> OTHER INFORMATION: probe binding region for Snapback primer
<220> FEATURE:
<221> NAME/KEY: primer_bind
<222> LOCATION: (25)..(44)

<400> SEQUENCE: 32
acaatattta tgacgattcc gcagatgttt agactggata gcgt        44

<210> SEQ ID NO 33
<211> LENGTH: 44
<212> TYPE: DNA
<213> ORGANISM: Artificial Sequence
<220> FEATURE:
<223> OTHER INFORMATION: primer for artificial plasmid
<220> FEATURE:
<221> NAME/KEY: misc_feature
<222> LOCATION: (1)..(2)
<223> OTHER INFORMATION: two base mismatch
<220> FEATURE:
<221> NAME/KEY: misc_binding
<222> LOCATION: (3)..(24)
<223> OTHER INFORMATION: probe binding region for Snapback primer
<220> FEATURE:
<221> NAME/KEY: primer_bind
<222> LOCATION: (25)..(44)

<400> SEQUENCE: 33
gctcaatgaa tatttatgac gattatgttt agactggata gcgt        44

<210> SEQ ID NO 34
<211> LENGTH: 44
<212> TYPE: DNA
<213> ORGANISM: Artificial Sequence
<220> FEATURE:
<223> OTHER INFORMATION: primer for artificial plasmid
<220> FEATURE:
<221> NAME/KEY: misc_feature
<222> LOCATION: (1)..(2)
<223> OTHER INFORMATION: probe binding region for Snapback primer

```
<220> FEATURE:
<221> NAME/KEY: misc_binding
<222> LOCATION: (3)..(24)
<223> OTHER INFORMATION: probe binding region for Snapback primer
<220> FEATURE:
<221> NAME/KEY: primer_bind
<222> LOCATION: (25)..(44)

<400> SEQUENCE: 34
ctggggattc aatgaatatt tatgatgttt agactggata gcgt            44

<210> SEQ ID NO 35
<211> LENGTH: 44
<212> TYPE: DNA
<213> ORGANISM: Artificial Sequence
<220> FEATURE:
<223> OTHER INFORMATION: primer for artificial plasmid
<220> FEATURE:
<221> NAME/KEY: misc_feature
<222> LOCATION: (1)..(2)
<223> OTHER INFORMATION: two base mismatch
<220> FEATURE:
<221> NAME/KEY: misc_binding
<222> LOCATION: (3)..(24)
<223> OTHER INFORMATION: probe binding region for Snapback primer
<220> FEATURE:
<221> NAME/KEY: primer_bind
<222> LOCATION: (25)..(44)

<400> SEQUENCE: 35
agtttgaggg ggattcaatg aataatgttt agactggata gcgt            44

<210> SEQ ID NO 36
<211> LENGTH: 22
<212> TYPE: DNA
<213> ORGANISM: Homo sapiens
<220> FEATURE:
<221> NAME/KEY: primer_bind
<222> LOCATION: (1)..(22)

<400> SEQUENCE: 36
tgtgcctttc aaattcagat tg                                    22

<210> SEQ ID NO 37
<211> LENGTH: 46
<212> TYPE: DNA
<213> ORGANISM: Artificial Sequence
<220> FEATURE:
<223> OTHER INFORMATION: contains several sequences from Homo sapiens
      CFTR gene
<220> FEATURE:
<221> NAME/KEY: misc_feature
<222> LOCATION: (1)..(2)
<223> OTHER INFORMATION: two base mismatch
<220> FEATURE:
<221> NAME/KEY: misc_binding
<222> LOCATION: (3)..(26)
<223> OTHER INFORMATION: probe binding region for Snapback primer
<220> FEATURE:
<221> NAME/KEY: primer_bind
<222> LOCATION: (27)..(46)

<400> SEQUENCE: 37
ctgaaagaca atatagttct tggagacagc aaatgcttgc tagacc          46

<210> SEQ ID NO 38
<211> LENGTH: 21
<212> TYPE: DNA
<213> ORGANISM: Homo sapiens
<220> FEATURE:
<221> NAME/KEY: primer_bind
```

```
<222> LOCATION: (1)..(21)

<400> SEQUENCE: 38
acttctaatg atgattatgg g                                              21

<210> SEQ ID NO 39
<211> LENGTH: 50
<212> TYPE: DNA
<213> ORGANISM: Artificial Sequence
<220> FEATURE:
<223> OTHER INFORMATION: contains several sequences from Homo sapiens
      CFTR gene
<220> FEATURE:
<221> NAME/KEY: misc_feature
<222> LOCATION: (1)..(2)
<223> OTHER INFORMATION: two base mismatch
<220> FEATURE:
<221> NAME/KEY: misc_binding
<222> LOCATION: (3)..(30)
<223> OTHER INFORMATION: probe binding region for Snapback primer
<220> FEATURE:
<221> NAME/KEY: primer_bind
<222> LOCATION: (31)..(50)

<400> SEQUENCE: 39
tcaatatcat ctttggtgtt tcctatgatg acatagtttc ttacctcttc               50

<210> SEQ ID NO 40
<211> LENGTH: 20
<212> TYPE: DNA
<213> ORGANISM: Artificial Sequence
<220> FEATURE:
<223> OTHER INFORMATION: primer for artificial plasmid
<220> FEATURE:
<221> NAME/KEY: primer_bind
<222> LOCATION: (1)..(20)

<400> SEQUENCE: 40
atgtttagac tggatagcgt                                                20

<210> SEQ ID NO 41
<211> LENGTH: 24
<212> TYPE: DNA
<213> ORGANISM: Artificial Sequence
<220> FEATURE:
<223> OTHER INFORMATION: probe for artificial plasmid
<220> FEATURE:
<221> NAME/KEY: misc_binding
<222> LOCATION: (1)..(24)
<223> OTHER INFORMATION: probe
<220> FEATURE:
<221> NAME/KEY: misc_feature
<222> LOCATION: (1)..(1)
<223> OTHER INFORMATION: fluorophore bound

<400> SEQUENCE: 41
ggattcaatg aatatttatg acga                                           24

<210> SEQ ID NO 42
<211> LENGTH: 30
<212> TYPE: DNA
<213> ORGANISM: Homo sapiens
<220> FEATURE:
<221> NAME/KEY: primer_bind
<222> LOCATION: (1)..(30)

<400> SEQUENCE: 42
tctcagggta ttttatgaga aataaatgaa                                     30
```

```
<210> SEQ ID NO 43
<211> LENGTH: 45
<212> TYPE: DNA
<213> ORGANISM: Artificial Sequence
<220> FEATURE:
<223> OTHER INFORMATION: contains several sequence for Homo sapiens
      CFTR gene
<220> FEATURE:
<221> NAME/KEY: misc_feature
<222> LOCATION: (1)..(2)
<223> OTHER INFORMATION: two-base mismatch
<220> FEATURE:
<221> NAME/KEY: misc_binding
<222> LOCATION: (3)..(20)
<223> OTHER INFORMATION: probe binding region for Snapback primer
<220> FEATURE:
<221> NAME/KEY: primer_bind
<222> LOCATION: (21)..(45)

<400> SEQUENCE: 43
gtaaggagga acgctctatc tcctcacaat aataaagaga aggca                45
```